US012622955B2

(12) United States Patent
Aurisicchio et al.

(10) Patent No.: US 12,622,955 B2
(45) Date of Patent: May 12, 2026

(54) CONSENSUS SEQUENCE OF THE ANTIGEN TELOMERASE AND THE USE THEREOF IN PREVENTIVE AND THERAPEUTIC VACCINATION

(71) Applicant: EVVIVAX S.R.L., Rome (IT)

(72) Inventors: Luigi Aurisicchio, Rome (IT);
Antonella Conforti, Rome (IT)

(73) Assignee: EvviVax S.r.l., Rome (IT)

( * ) Notice: Subject to any disclaimer, the term of this patent is extended or adjusted under 35 U.S.C. 154(b) by 225 days.

(21) Appl. No.: 18/018,541

(22) PCT Filed: Jul. 26, 2021

(86) PCT No.: PCT/IT2021/050227
§ 371 (c)(1),
(2) Date: Jan. 27, 2023

(87) PCT Pub. No.: WO2022/024156
PCT Pub. Date: Feb. 3, 2022

(65) Prior Publication Data
US 2025/0152687 A1    May 15, 2025

(30) Foreign Application Priority Data
Jul. 29, 2020    (IT) ........................ 102020000018379

(51) Int. Cl.
*A61K 39/00* (2006.01)
*A61P 35/00* (2006.01)
*C12N 9/12* (2006.01)

(52) U.S. Cl.
CPC ...... *A61K 39/001157* (2018.08); *A61P 35/00* (2018.01); *C12N 9/1276* (2013.01);
(Continued)

(58) Field of Classification Search
CPC ........ A61K 39/001157; A61K 2039/53; A61K 2039/572; A61K 2039/552; A61P 35/00;
(Continued)

(56) References Cited

U.S. PATENT DOCUMENTS

| | | | |
|---|---|---|---|
| 2008/0038250 A1* | 2/2008 | Zlatkin .................. | C07K 14/44 435/6.12 |
| 2016/0046950 A1* | 2/2016 | Langlade Demoyen .................... | C12N 15/52 536/23.2 |
| 2020/0030426 A1* | 1/2020 | Weiner .................. | A61K 39/39 |

FOREIGN PATENT DOCUMENTS

| | | |
|---|---|---|
| WO | WO 2014/154904 A1 | 10/2014 |
| WO | WO 2014/154905 A1 | 10/2014 |

OTHER PUBLICATIONS

Pyo et al., Immune adjuvant effect of a Toxoplasma gondii profilin-like protein in autologous whole-tumor-cell vaccination in mice, Oncotarget, (2016) vol. 7, No. 45, p. 74107-74119 (Year: 2016).*
(Continued)

*Primary Examiner* — Robert B Mondesi
*Assistant Examiner* — Naghmeh Nina Moazzami
(74) *Attorney, Agent, or Firm* — Knobbe, Martens, Olson & Bear LLP

(57) ABSTRACT

A consensus sequence of the antigen telomerase (ConTRt) can be generated and used in preventive and therapeutic vaccination. The consensus sequence of telomerase was generated by the fusion of two sequences, one belonging to human telomerase (hTERT) and the other to dog telomerase (dTERT), with the aim of developing an effective vaccine for the treatment of tumors expressing both human and dog telomerase, hence in both the human and veterinary sectors.

11 Claims, 8 Drawing Sheets
Specification includes a Sequence Listing.

(52) U.S. Cl.
CPC .... *A61K 2039/53* (2013.01); *A61K 2039/572*
(2013.01); *C07K 2319/30* (2013.01); *C07K*
*2319/55* (2013.01); *C12Y 207/07049* (2013.01)
(58) Field of Classification Search
CPC .............. C12N 9/1276; C07K 2319/30; C07K
2319/55; C07K 2319/00; C07K 2319/02;
C12Y 207/07049
See application file for complete search history.

(56) References Cited

OTHER PUBLICATIONS

T03844 and Nakamura et al. (PIR database, Nakamura et al., Telomerase catalytic subunit homologs from fission yeast and human Apr. 1997 (Year: 1997).*

J. Yan et al, "Highly Optimized DNA Vaccine Targeting Human Telomerase Reverse Transcriptase Stimulates Potent Antitumor Immunity", Cancer Immunology Research, vol. 1, No. 3, Jul. 17, 2013 (Jul. 17, 2013).

International Search Report & Written Opinion issued Mar. 28, 2022; in PCT/IT2021/050227, which is related to the present application.

Akincilar, et al., "Reactivation of telomerase in cancer", Cell. Mol. Life Sci. (2016) 73:1659-1670 DOI 10.1007/s00018-016-2146-9.

Bergmana, et al., "Development of a xenogeneic DNA vaccine program for canine malignant melanoma at the Animal Medical Center" Vaccine 24 (2006) 4582-4585.

Bird, "Maintaining tolerance" Nature Publishing Group, Jun. 2005, vol. 5, p. 432.

Cavallo, et al. "Xenogene vaccination in the therapy of cancer", Expert Opin. Biol. Ther. (2014) 14(10).

Dharmapuri, et al. "Coadministration of Telomerase Genetic Vaccine and a Novel TLR9 Agonist in Nonhuman Primates", www. moleculartherapy.org vol. 17 No. 10, 1804-1813 Oct. 2009.

Eriksson, et al. "DNA vaccine coding for the rhesus prostate specific antigen delivered by intradermal electroporation in patients with relapsed prostate cancer", Vaccine 31 (2013) 3843-3848.

Fattori, et al., "ErbB2 Genetic Cancer Vaccine in Nonhuman Primates; Relevance of Single Nucleotide Polymorphisms" Human Gene Therapy 20:253-265 (Mar. 2009) Mary Ann Liebert, Inc. DOI: 10.1089=hum.2008.153.

Gavazza, et al., "Safety and Efficacy of a Genetic Vaccine Targeting Telomerase Plus Chemotherapy for the Therapy of Canine B-Cell Lymphoma", Human Gene Therapy 24:728-738 (Aug. 2013) Mary Ann Liebert, Inc. DOI: 0.1089/hum.2013.112.

Ginsberg, et al., "Immunologic Response to Xenogeneic gp100 DNA in Melanoma Patients: Comparison of Particle Mediated Epidermal Delivery with Intramuscular Injection", Clin Cancer Res. Aug. 1, 2010; 16(15): 4057-4065. doi:10.1158/1078-0432.CCR-10-1093.

Impellizeri, et al. "Electro-gene-transfer as a new tool for cancer immunotherapy in animals", 2012 Blackwell Publishing Ltd, Veterinary and Comparative Oncology, doi: 10.1111/vco.12006.

Jacob, et al. "Activity of DNA vaccines encoding self or heterologous Her-2/neu in Her-2 or neu transgenic mice", Cellular Immunology 240 (2006) 96-106.

Kailashiya, "Telomerase based anticancer immunotherapy and vaccines approaches" http://dx.doi.org/10.1016/j.vaccine.2017.09.011.

Liu, et al. "Tumour-associated antigens and their anti-cancer applications", 2016 John Wiley & Sons Ltd. European Journal of Cancer Care, DOI: 10.1111/ecc.12446.

Nasir, et al. "Telomeres and telomerase: Biological and clinical importance in dogs", The Veterinary Journal 175 (2008) 155-163 doi:10.1016/j.tvjl.2007.01.024.

Peruzzi, et al. "A Vaccine Targeting Telomerase Enhances Survival of Dogs Affected by B-cell Lymphoma", Molecular Therapy vol. 18 No. 8, 1559-1567 / Aug. 2010 http://www.nature.com/doifinder/10.1038/mt.2010.104.

Quaglino, et al. "A Better Immune Reaction to Erbb-2 Tumors Is Elicited in Mice by DNA Vaccines Encoding Rat/Human Chimeric Proteins" Cancer Res; 70(7) Apr. 1, 2010, doi: 10.1158/0008-5472.CAN-09-2548.

Riccardo, et al. "CSPG4-specific immunity and survival prolongation in dogs with oral malignant melanoma immunized with human CSPG4 DNA", Clin Cancer Res. Jul. 15, 2014; 20(14): 3753-3762. doi:10.1158/1078-0432.CCR-13-3042.

Seremet, et al. "Tumor-Specific Antigens and Immunologic Adjuvants in Cancer Immunotherapy", The Cancer Journal & vol. 17, No. 5, Sep./Oct. 2011.

Teixeira, et al. "A First-in-Human Phase I Study of INVAC-1, an Optimized Human Telomerase DNA Vaccine in Patients with Advanced Solid Tumors" American Association for Cancer Research, Sep. 26, 2019; DOI: 10.1158/1078-0432.CCR-19-1614.

Thalmensi, et al. "Anticancer DNA vaccine based on human telomerase reverse transcriptase generates a strong and specific T cell immune response", Onicoimmunology 2016, vol. 5, No. 3, e 1083670, 11 pages. http://dx.doi.org/10.1080/2162402X.2015.1083670.

Thalmensi, et al. "A DNA telomerase vaccine for canine cancer immunotherapy", Oncotarget, 2019, vol. 10, (No. 36), pp. 3361-3372.

Vonderheide, Telomerase as a universal tumor-associated antigen for cancer Immunotherapy Oncogene (2002) 21, 674-679.

Yan, et al. "Highly optimized DNA vaccine targeting human telomerase reverse transcriptase stimulates potent antitumor immunity", Cancer Immunol Res. Sep. 2013 ; 1(3): 179-189. doi:10.1158/2326-6066. CIR-13-0001.

Yu, et al. "Chicken HSP70 DNA vaccine inhibits tumor growth in a canine cancer model", Vaccine 29 (2011) 3489-3500.

* cited by examiner

```
           1                                                            50
   hTERT   MPRAPRCRAV RSLLRSHYRE VLPLATFVRR LGPQGWRLVQ RGDPAAFRAL
    HuCa   .PRAPRCRAV RSLLRSHYRE VLPLATFVRR LGPQGWRLVQ RGDPAAFRAL
 dogTERT   MPRAPRCRAV RALLRGRYRE VLPLATFLRR LGPPGRLLVR RGDPAAFRAL
    CaHu   MPRAPRCRAV RALLRGRYRE VLPLATFLRR LGPPGRLLVR RGDPAAFRAL
  ConTRT   mPRAPRCRAV RaLLRghYRE VLPLATF1RR LGPpGr1lVq RGDPAAFRAL 51                                                           100
   hTERT   VAQCLVCVPW DARPPPAAPS FRQVSCLKEL VARVLQRLCE RGAKNVLAFG
    HuCa   VAQCLVCVPW DARPPPAAPS FRQVSCLKEL VARVLQRLCE RGAKNVLAFG
 dogTERT   VAQCLVCVPW GARPPPAAPC FRQVSCLKEL VARVVQRLCE RGARNVLAFG
    CaHu   VAQCLVCVPW GARPPPAAPC FRQVSCLKEL VARVVQRLCE RGARNVLAFG
  ConTRT   VAQCLVCVPW dARPPPAAPc FRQVSCLKEL VARV1QRLCE RGAkNVLAFG 101                                                           150
   hTERT   FALLDGARGG PPEAFTTSVR SYLPNTVTDA LRGSGAWGLL LRRVGDDVLV
    HuCa   FALLDGARGG PPEAFTTSVR SYLPNTVTDA LRGSGAWGLL LRRVGDDVLV
 dogTERT   FALLDGARGG PPVAFTTSVR SYLPNTVTET LRGSGAWGLL LRRVGDDVLT
    CaHu   FALLDGARGG PPVAFTTSVR SYLPNTVTET LRGSGAWGLL LRRVGDDVLT
  ConTRT   FALLDGARGG PPeAFTTSVR SYLPNTVTda LRGSGAWGLL LRRVGDDVLt 151                                                           200
   hTERT   HLLARCALFV LVAPSCAYQV CGPPLYQLGA ATQARPPPHA SGPRRRLGCE
    HuCa   HLLARCALFV LVAPSCAYQV CGPPLYQLGA ATQARPPPHA SGPRRRLGCE
 dogTERT   HLLARCALYL LVAPSCAYQV CGPPLYDLCA PASLPLPAPG LPGLPGLPGL
    CaHu   HLLARCALYL LVAPSCAYQV CGPPLYDLCA PASLPLPAPG LPGLPGLPGL
  ConTRT   HLLARCALfl LVAPSCAYQV CGPPLYdLcA aaqaplPaha lgglpglgce 201                                                           250
   hTERT   RAWNHSVREA GVPLGLPAPG ARRRGGSASR SLPLPKRPRR GAAPEPERTP
    HuCa   RAWNHSVREA GVPLGLPAPG ARRRGGSASR SLPLPKRPRR GAAPEPERTP
 dogTERT   GAGAGASADL RPTRQAQNSG ARRRGSPGS GVPLAKRPRR SVASEPER..
    CaHu   GAGAGASADL RPTRQAQNSG ARRRGSPGS GVPLAKRPRR SVASEPER..
  ConTRT   gAgagasada gpplgapapG ARRRgGSagr glPLaKRPRR gaApEPER..
```

Fig. 1 hTERT: SEQ ID NO:29
HuCa: SEQ ID NO:3
dogTERT: SEQ ID NO:30
CaHu: SEQ ID NO:2
ConTERT: SEQ ID NO:1

```
          251                                                        300
   hTERT  VGQGSWAHPG  RTRGPSDRGF  CVVSPARPAE  EATSLEGALS  GTRHSHPSVG
   HuCa   VGQGSWAHPG  RTRGPSDRGF  CVVSPARPAE  EATSLEGALS  GTRHSHPSVG
 dogTERT  ...GAHRSFP  RAQQPPVSEA  PAVTPAVAAS  PAASWEGGPP  GTRPTTPAWH
   CaHu   ...GAHRSFP  RAQQPPVSEA  PAVTPAVAAS  PAASWEGGPP  GTRPTTPAWH
 ConTRT   ...Gahahfg  RaqgPpdrea  caVsPAraAe  eAaSlEGalp  GTRhshPavg 301                                                        350
   hTERT  RQHHAGPPST  SRPPRPWDTP  CPPVYAETKH  FLYSSGDKEQ  LRPSFLLSSL
   HuCa   RQHHAGPPST  SRPPRPWDTP  CPPVYAETKH  FLYSSGDKEQ  LRPSFLLSSL
 dogTERT  PY........  ...PGPQGVP  HDPAHPETKR  FLYCSGGRER  LRPSFLLSAL
   CaHu   PY........  ...PGPQGVP  HDPAHPETKR  FLYCSGGRER  LRPSFLLSAL
 ConTRT   pq........  ...PgPqdtP  cdPahaETKh  FLYcSGdkEq  LRPSFLLSaL 351                                                        400
   hTERT  RPSLTGARRL  VETIFLGSRP  WMPGTPRRLP  RLPQRYWQMR  PLFLELLGNH
   HuCa   RPSLTGARRL  VETIFLGSRP  WMPGTPRRLP  RLPQRYWQMR  PLFLELLGNH
 dogTERT  PPTLSGARKL  VETIFLGSAP  QKPGAARRMR  RLPARYWRMR  PLFQELLGNH
   CaHu   PPTLSGARKL  VETIFLGSAP  QKPGAARRMR  RLPARYWRMR  PLFQELLGNH
 ConTRT   pPsLsGARkL  VETIFLGSaP  qkPGaaRRlp  RLPaRYWqMR  PLFlELLGNH 401                                                        450
   hTERT  AQCPYGVLLK  THCPLRAAVT  PA.....AGV  CAREKPQGSV  AAPEEEDTDP
   HuCa   AQCPYGVLLK  THCPLRAAVT  PA.....AGV  CAREKPQGSV  AAPEEEDTDP
 dogTERT  ARCPYRALLR  THCPLRAMAA  KEGSGNQAHR  GVGICPLERP  VAAPQEQTDS
   CaHu   ARCPYRALLR  THCPLRAMAA  KEGSGNQAHR  GVGICPLERP  VAAPQEQTDS
 ConTRT   AqCPYgaLLk  THCPLRAaaa  ka.....Agr  cagecPlerp  aAaeeEdTDp 451                                                        500
   hTERT  RRLVQLLRQH  SSPWQVYGFV  RACLRRLVPP  GLWGSRHNER  RFLRNTKKFI
   HuCa   RRLVQLLRQH  SSPWQVYGFV  RACLRRLVPP  GLWGSRHNER  RFLRNTKKFI
 dogTERT  TRLVQLLRQH  SSPWQVYAFL  RACLCWLVPT  GLWGSRHNQR  RFLRNVKKFI
   CaHu   TRLVQLLRQH  SSPWQVYAFL  RACLCWLVPT  GLWGSRHNQR  RFLRNVKKFI
 ConTRT   rRLVQLLRQH  SSPWQVYaFl  RACLcrLVPp  GLWGSRHNeR  RFLRNtKKFI
```

Fig. 1 (continued)

```
           501                                                   550
    hTERT  SLGKHAKLSL QELTWKMSVR DCAWLRRSPG VGCVPAAEHR LREEILAKFL
     HuCa  SLGKHAKLSL QELTWKMSVR DCAWLRRSPG VGCVPAAEHR LREEILAKFL
  dogTERT  SLGKHAKLSL QELTWKMKVR DCTWLHGNPG ACCVPAAEHR RREEILARFL
     CaHu  SLGKHAKLSL QELTWKMKVR DCTWLHGNPG ACCVPAAEHR RREEILARFL
   ConTRT  SLGKHAKLSL QELTWKMkVR DCaWLhgnPG acCVPAAEHR lREEILAkFL 551                                                   600
    hTERT  HWLMSV.YVV ELLRSFFYVT ETTFQKNRLF FYRKSVWSKL QSIGIRQHLK
     HuCa  HWLMSV.YVV ELLRSFFYVT ETTFQKNRLF FYRKSVWSKL QSIGIRQHLK
  dogTERT  VLVDGHIYVV KLLRSFFYVT ETTFQKNRLF FYRKSVWSQL QSIGIRQLFN
     CaHu  VLVDGHIYVV KLLRSFFYVT ETTFQKNRLF FYRKSVWSQL QSIGIRQLFN
   ConTRT  hlldgh.YVV eLLRSFFYVT ETTFQKNRLF FYRKSVWSkL QSIGIRQhfk 601                                                   650
    hTERT  RVQLRELSEA EVRQHREARP ALLTSRLRFI PKPDGLRPIV NMDYVVGART
     HuCa  RVQLRELSEA EVRQHREARP ALLTSRLRFI PKPDGLRPIV NMDYVVGART
  dogTERT  SVHLRELSEA EVRRHREARP ALLTSRLRFL PKPSGLRPIV NMDYIMGART
     CaHu  SVHLRELSEA EVRRHREARP ALLTSRLRFL PKPSGLRPIV NMDYIMGART
   ConTRT  rVhLRELSEA EVRqHREARP ALLTSRLRFi PKPdGLRPIV NMDYimGART 651                                                   700
    hTERT  FRREKRAERL TSRVKALFSV LNYERARRPG LLGASVLGLD DIHRAWRTFV
     HuCa  FRREKRAERL TSRVKALFSV LNYERARRPG LLGASVLGLD DIHRAWRTFV
  dogTERT  FHRDKKVQHL TSQLKTLFSV LNYERARRPS LLGASMLGMD DIHRAWRTFV
     CaHu  FHRDKKVQHL TSQLKTLFSV LNYERARRPS LLGASMLGMD DIHRAWRTFV
   ConTRT  FhRdKkaehl TSqlKaLFSV LNYERARRPg LLGASmLG1D DIHRAWRTFV 701                                                   750
    hTERT  LRVRAQDPPP ELYFVKVDVT GAYDTIPQDR LTEVIASIIK PQN.TYCVRR
     HuCa  LRVRAQDPPP ELYFVKVAIT GAYDALPQDR LVEVIANVIR PQESTYCVRH
  dogTERT  LRIRAQNPAP QLYFVKVAIT GAYDALPQDR LVEVIANVIR PQESTYCVRH
     CaHu  LRIRAQNPAP QLYFVKVAIT GAYDTIPQDR LTEVIASIIK PQN.TYCVRR
   ConTRT  LRiRAQdPaP eLYFVKVaiT GAYDaiPQDR LtEVIAniIk PQe.TYCVRh
```

Fig. 1 (continued)

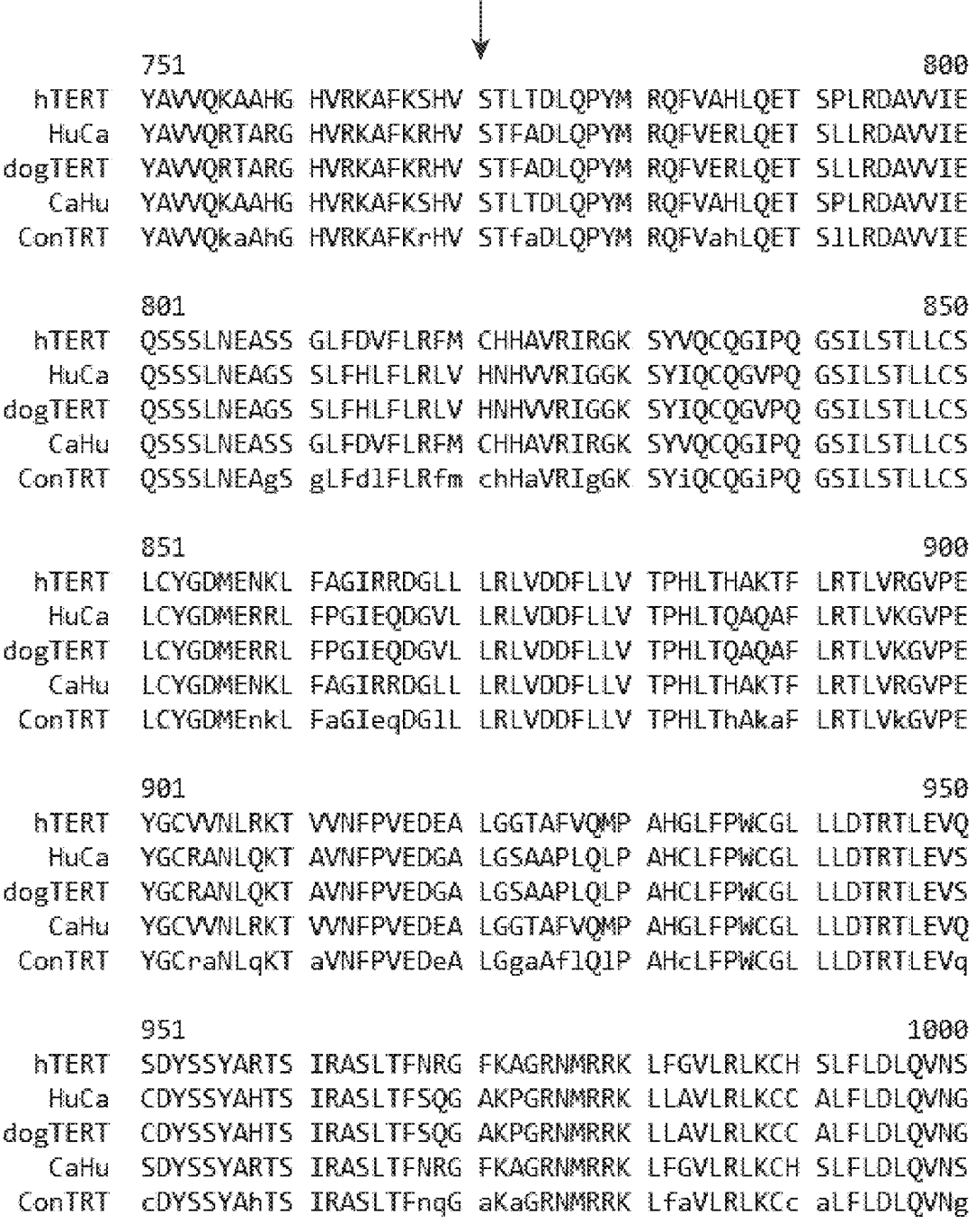

```
        751                                                    800
 hTERT  YAVVQKAAHG  HVRKAFKSHV  STLTDLQPYM  RQFVAHLQET  SPLRDAVVIE
  HuCa  YAVVQRTARG  HVRKAFKRHV  STFADLQPYM  RQFVERLQET  SLLRDAVVIE
dogTERT YAVVQRTARG  HVRKAFKRHV  STFADLQPYM  RQFVERLQET  SLLRDAVVIE
  CaHu  YAVVQKAAHG  HVRKAFKSHV  STLTDLQPYM  RQFVAHLQET  SPLRDAVVIE
 ConTRT YAVVQkaAhG  HVRKAFKrHV  STfaDLQPYM  RQFVahLQET  SlLRDAVVIE 801                                                    850
 hTERT  QSSSLNEASS  GLFDVFLRFM  CHHAVRIRGK  SYVQCQGIPQ  GSILSTLLCS
  HuCa  QSSSLNEAGS  SLFHLFLRLV  HNHVVRIGGK  SYIQCQGVPQ  GSILSTLLCS
dogTERT QSSSLNEAGS  SLFHLFLRLV  HNHVVRIGGK  SYIQCQGVPQ  GSILSTLLCS
  CaHu  QSSSLNEASS  GLFDVFLRFM  CHHAVRIRGK  SYVQCQGIPQ  GSILSTLLCS
 ConTRT QSSSLNEAgS  gLFdlFLRfm  chHaVRIgGK  SYiQCQGiPQ  GSILSTLLCS 851                                                    900
 hTERT  LCYGDMENKL  FAGIRRDGLL  LRLVDDFLLV  TPHLTHAKTF  LRTLVRGVPE
  HuCa  LCYGDMERRL  FPGIEQDGVL  LRLVDDFLLV  TPHLTQAQAF  LRTLVKGVPE
dogTERT LCYGDMERRL  FPGIEQDGVL  LRLVDDFLLV  TPHLTQAQAF  LRTLVKGVPE
  CaHu  LCYGDMENKL  FAGIRRDGLL  LRLVDDFLLV  TPHLTHAKTF  LRTLVRGVPE
 ConTRT LCYGDMEnkL  FaGIeqDGlL  LRLVDDFLLV  TPHLThAkaF  LRTLVkGVPE 901                                                    950
 hTERT  YGCVVNLRKT  VVNFPVEDEA  LGGTAFVQMP  AHGLFPWCGL  LLDTRTLEVQ
  HuCa  YGCRANLQKT  AVNFPVEDGA  LGSAAPLQLP  AHCLFPWCGL  LLDTRTLEVS
dogTERT YGCRANLQKT  AVNFPVEDGA  LGSAAPLQLP  AHCLFPWCGL  LLDTRTLEVS
  CaHu  YGCVVNLRKT  VVNFPVEDEA  LGGTAFVQMP  AHGLFPWCGL  LLDTRTLEVQ
 ConTRT YGCraNLqKT  aVNFPVEDeA  LGgaAflQlP  AHcLFPWCGL  LLDTRTLEVq 951                                                   1000
 hTERT  SDYSSYARTS  IRASLTFNRG  FKAGRNMRRK  LFGVLRLKCH  SLFLDLQVNS
  HuCa  CDYSSYAHTS  IRASLTFSQG  AKPGRNMRRK  LLAVLRLKCC  ALFLDLQVNG
dogTERT CDYSSYAHTS  IRASLTFSQG  AKPGRNMRRK  LLAVLRLKCC  ALFLDLQVNG
  CaHu  SDYSSYARTS  IRASLTFNRG  FKAGRNMRRK  LFGVLRLKCH  SLFLDLQVNS
 ConTRT cDYSSYAhTS  IRASLTFnqG  aKaGRNMRRK  LfaVLRLKCc  aLFLDLQVNg
```

Fig. 1 (continued)

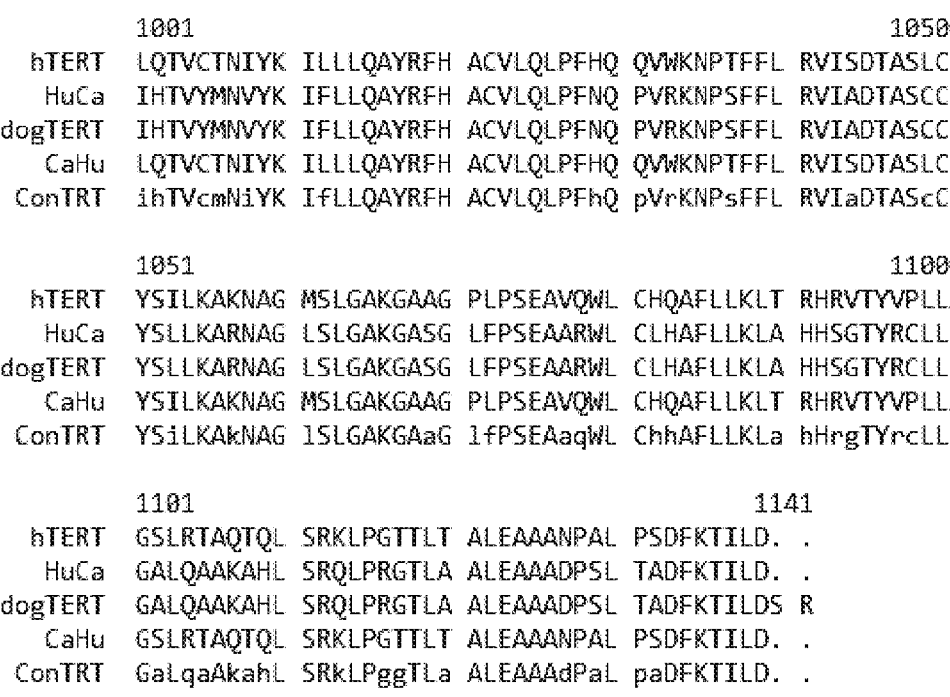

```
              1001                                                    1050
    hTERT     LQTVCTNIYK  ILLLQAYRFH  ACVLQLPFHQ  QVWKNPTFFL  RVISDTASLC
    HuCa      IHTVYMNVYK  IFLLQAYRFH  ACVLQLPFNQ  PVRKNPSFFL  RVIADTASCC
    dogTERT   IHTVYMNVYK  IFLLQAYRFH  ACVLQLPFNQ  PVRKNPSFFL  RVIADTASCC
    CaHu      LQTVCTNIYK  ILLLQAYRFH  ACVLQLPFHQ  QVWKNPTFFL  RVISDTASLC
    ConTRT    ihTVcmNiYK  IfLLQAYRFH  ACVLQLPFhQ  pVrKNPsFFL  RVIaDTAScC 1051                                                    1100
    hTERT     YSILKAKNAG  MSLGAKGAAG  PLPSEAVQWL  CHQAFLLKLT  RHRVTYVPLL
    HuCa      YSLLKARNAG  LSLGAKGASG  LFPSEAARWL  CLHAFLLKLA  HHSGTYRCLL
    dogTERT   YSLLKARNAG  LSLGAKGASG  LFPSEAARWL  CLHAFLLKLA  HHSGTYRCLL
    CaHu      YSILKAKNAG  MSLGAKGAAG  PLPSEAVQWL  CHQAFLLKLT  RHRVTYVPLL
    ConTRT    YSiLKAkNAG  lSLGAKGAaG  lfPSEAaqWL  ChhAFLLKLa  hHrgTYrcLL 1101                                                    1141
    hTERT     GSLRTAQTQL  SRKLPGTTLT  ALEAAANPAL  PSDFKTILD.  .
    HuCa      GALQAAKAHL  SRQLPRGTLA  ALEAAADPSL  TADFKTILD.  .
    dogTERT   GALQAAKAHL  SRQLPRGTLA  ALEAAADPSL  TADFKTILDS  R
    CaHu      GSLRTAQTQL  SRKLPGTTLT  ALEAAANPAL  PSDFKTILD.  .
    ConTRT    GaLqaAkahL  SRkLPggTLa  ALEAAAdPaL  paDFKTILD.  .
```

Fig. 1 (continued)

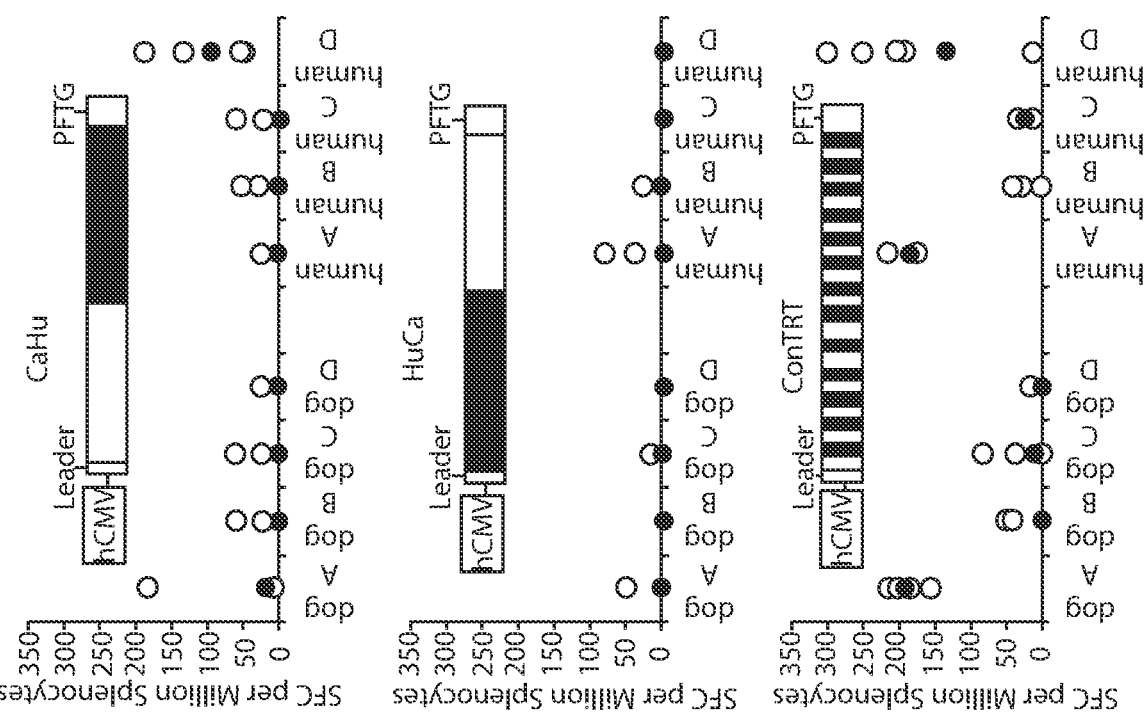
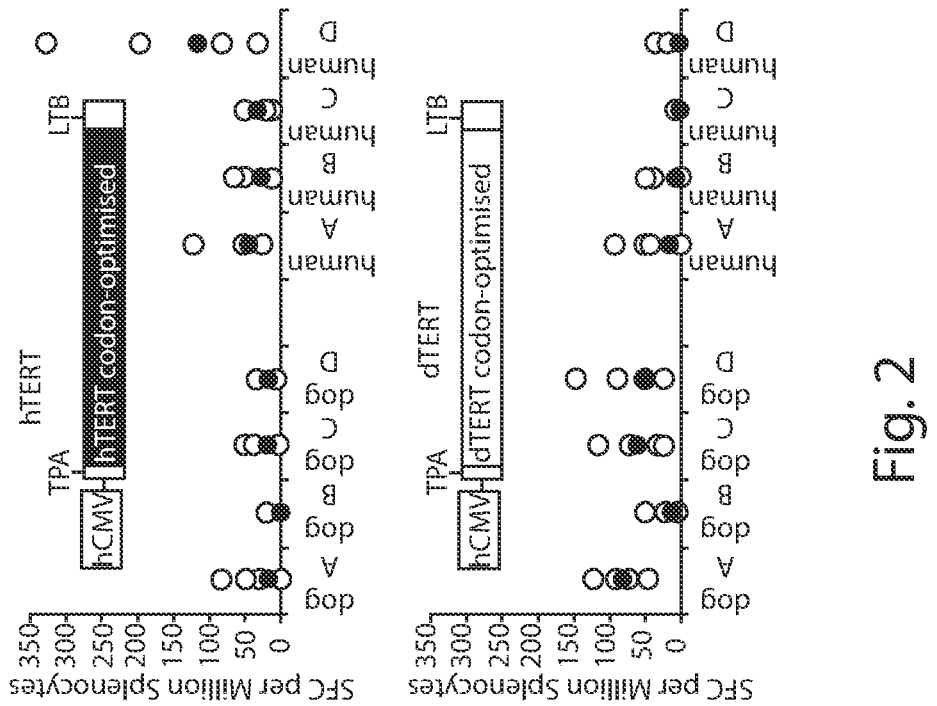
Fig. 2

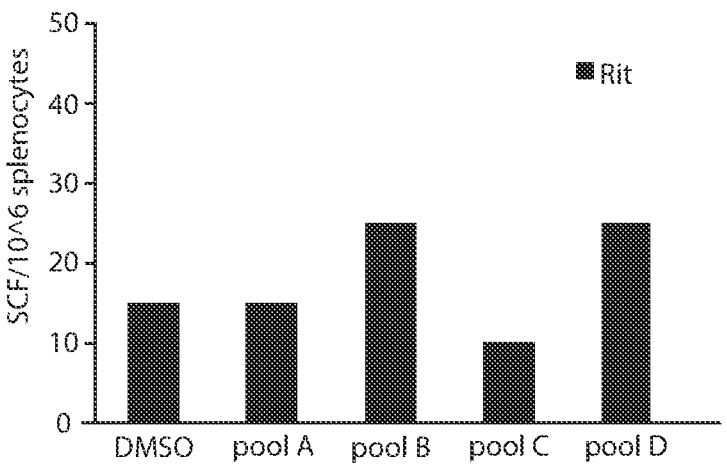
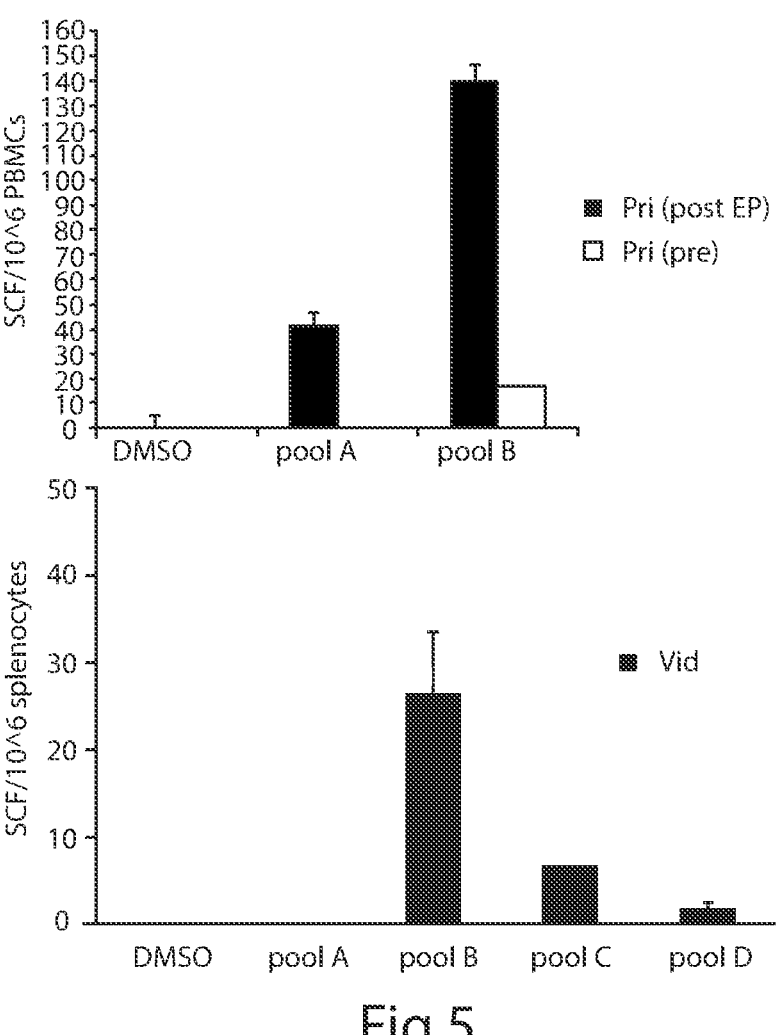
Fig.5

CONSENSUS SEQUENCE OF THE ANTIGEN TELOMERASE AND THE USE THEREOF IN PREVENTIVE AND THERAPEUTIC VACCINATION

PRIORITY AND CROSS REFERENCE TO RELATED APPLICATIONS

This application is the U.S. National Phase Application under 35 U.S.C. § 371 of International Application No. PCT/IT2021/050227, filed Jul. 26, 2021, and published as WO2022/024156A2 on Feb. 3, 2022, which claims the benefit of Foreign Application No. IT102020000018379, filed Jul. 29, 2020. Any and all applications for which a foreign or a domestic priority is claimed is/are identified in the Application Data Sheet filed herewith and is/are hereby incorporated by reference in their entireties under 37 C.F.R. § 1.57.

REFERENCE TO SEQUENCE LISTING

The present application is being filed along with a Sequence Listing in electronic format. The Sequence Listing is provided as a file entitled SequenceListing BARZ070.001APC.txt, created Jan. 26, 2023, which is approximately 84 kilobytes in size, which is replaced by a Replacement Electronic Sequence Listing submitted as herewith a file entitled BARZ070.001ACPCorrectedSequenceListing.txt, which is 76,442 bytes in size and was created on Jul. 17, 2024. The information in the electronic format of the Sequence Listing is incorporated herein by reference in its entirety.

FIELD

The present invention relates to a consensus sequence of the antigen telomerase and the use thereof in preventive and therapeutic vaccination. In particular, the present invention relates to the generation of a consensus sequence of the antigen telomerase (ConTRt) and the use thereof in preventive and therapeutic vaccination, wherein the telomerase consensus sequence was generated by the fusion of two sequences, one belonging to human telomerase (hTERT) and the other to dog telomerase (dTERT), with the aim of developing an effective vaccine for the treatment of tumours expressing both human and dog telomerase, hence in both the human and veterinary sectors.

BACKGROUND

It is well known that vaccination is a powerful tool for obtaining the activation of the immune system against pathogens of every type. Vaccination represents the first-line preventive intervention for eliminating the risk of contracting dangerous infectious diseases which can spread throughout a large part of the population, at times causing true epidemics. At present, thanks to vaccines it is possible to defeat highly dangerous infectious diseases for which a therapy either does not exist (poliomyelitis and hepatitis B) or is not always effective (diphtheria, tetanus) or diseases that can be a cause of serious complications (measles, German measles and whooping cough).

Immunotherapy, i.e. the therapeutic treatment of disease by means of an activation or suppression of the immune system, has demonstrated to be effective also against various types of tumours, despite having to overcome several limitations, such as immunological tolerance and low immunogenicity. The objective of tumour immunotherapy is therefore to restore the ability of the immune system to recognise tumour cells and eliminate them effectively, by overcoming the mechanisms whereby tumours suppress the immune response. To this end, the immune system recognises tumour-associated molecules (tumour-associated antigens) [Liu 2017], which, despite also being expressed by normal cells, appear on tumour cells in an abnormal manner in terms of quantity, site or time (for example, the carcinoembryonic antigen CEA) or molecules expressed exclusively by tumour cells (tumour-specific antigens), such as the products of normally silent genes [Seremet 2011]. Notwithstanding the discovery of tumour antigens as a target of immunotherapeutic strategies, the greatest obstacle in the development of cancer immunotherapy has been the absence of an antigen common to the majority of patients affected by the most common types of cancer, and thus different research groups have concentrated on the search for a universal tumour-associated antigen capable of inducing a T-cell response of a cytotoxic type (CTL) against a wide range of tumour types.

The tumour-associated antigen telomerase represents an ideal candidate for anti-tumour immunotherapy. Telomerase is an enzyme responsible for the lengthening of DNA telomeres, a phenomenon typical of actively proliferating cells, such as embryonal ones, and which is by contrast absent under physiological conditions in somatic cells. Under certain pathological conditions, in which proliferative activity increases, such as in neoplasms, telomerase activity also increases enormously, and various studies have by now demonstrated the correlation existing between telomerase activity and cancer [Akincilar 2016]. In addition to being expressed in about 90% of tumour types, telomerase is degraded by cellular proteasomes into peptides then presented in the context of MHC class I on the surface of the tumour cell as the target of the activity of antigen-specific cytotoxic T-cells. Considering the considerably lower levels of telomerase activity in somatic cells under physiological conditions, the number of specific MHC/TERT peptide complexes present at the level of the plasma membrane are insufficient to activate an immune response [Gross 2004], whereas the abnormal expression of telomerase in tumour cells enables the immune system to discriminate between normal tissue and neoplastic tissue, thus making telomerase an ideal candidate as a universal target antigen for an antitumour vaccine [Vonderheide 2002]. Furthermore, J. Yan et al., 2013, describe an optimised DNA vaccine that targets the reverse transcriptase of human telomerase, which should stimulate antitumour immunity [J. Yan et al. 2013].

Consequently, in recent years various phase I/II clinical studies have been started up in humans, with the aim of conducting experiments on antitumour vaccines targeting hTERT and based on peptides or autologous dendritic cells exhibiting the antigen telomerase [Kailashiya 2017]. However, such vaccines, despite the high immunogenicity and specificity for telomerase, are HLA-restricted and thus not potentially universal. In fact, to date such clinical studies have not yet achieved the hoped-for results, demonstrating a limited clinical impact on the majority of patients. Accordingly, in order to overcome such limitations, DNA vaccines targeting hTERT have been formulated, in consideration of the greater stability, ease of production and universal applicability of DNA [Dharmapuri 2009; Thalmensi 2016]. Furthermore, with the aim of improving their immunogenicity, new genetic vaccination methods have been conceived, e.g. electroporation, which have considerably increased the effectiveness of DNA vaccines, thus promoting experimentation therewith in phase I/II clinical studies in humans [Teixeira 2020].

In recent years, such therapeutic approaches have also been developed for the veterinary field. It is well known, in fact, that domestic animals, in particular dogs, develop tumours whose biology, incidence and response to therapies are similar to those of humans [Ranieri 2013]. Furthermore, unlike other species used as preclinical models (for example monkeys), dogs represent an excellent model 5 for studies on the effectiveness of antitumour therapies, considering the spontaneous onset and intrinsic interindividual heterogeneity of tumours, as occurs in humans. In dogs as well, furthermore, telomerase is expressed in over 90% of tumour types [Nasir 2008]. In various models of dog tumours expressing dTERT, clinical studies have thus been conducted which have demonstrated the effectiveness of genetic vaccines, in combination with chemotherapy treatment, in inducing a specific immune response to dTERT together with a greater antitumour effect and longer patient survival [Peruzzi 2010; Gavazza 2013; Thalmensi 2019]. Furthermore, also in this animal model, various strategies for administering the vaccine have been experimented with, including electroporation [Impellizeri 2012] and high pressure without the use of needles [Bergman 2006], the former method being capable of inducing a more powerful antigen-specific immune response than the latter [Yu 2011]. There are known immunogenic compositions comprising a nucleic acid which comprise a sequence encoding a cat or dog telomerase deprived of telomerase catalytic activity (WO2014/154904; WO2014/154905).

At present, only one genetic vaccine (Oncept®, distributed by Merial) directed against tyrosinase and used in the treatment of canine melanoma has been approved for sale by the USDA.

Therefore, in the light of the above, it appears evident that there is a need to provide more effective vaccination strategies which overcome the limits of the presently known methods for the treatment of telomerase-expressing tumours, in both the human and veterinary sectors.

It is well known that vaccination with a xenogeneic antigen, which shows a sufficient degree of homology with its ortholog, represents an effective method for obtaining more potent immune responses and overcoming tolerance towards self-proteins [Fattori 2009]. A particular example is offered by the xenogeneic DNA vaccination against ErbB2, a tyrosine kinase expressed in 20-30% of breast cancers and in different very aggressive types of epithelial tumours. In fact, the vaccine against the human form of ErbB2 (Her2) is capable of breaking immunological tolerance [Jacob 2006] in a model of transgenic mice with breast cancer expressing the rat form of ErbB2 (neu) due to the phenomenon of cross-reactivity [Cavallo 2014]. In particular, the autologous vaccine is capable of inducing antibodies towards the self-antigen, whereas the xenogeneic vaccine stimulates the activation of T-cells against the ortholog antigen. Consequently, in order to combine both immune system activation mechanisms, DNA sequences encoding for a chimeric rat/human or human/rat ErbB2 protein have been created, which has demonstrated to be able to induce potent responses against Her2/neu both in wild-type mice and in Her2/neu transgenic mice [Quaglino 2010]. The effectiveness of xenogeneic vaccination in breaking tolerance towards self-antigens and inducing an antitumour effect has been demonstrated in clinical studies conducted in humans [Ginsberg 2010; Eriksson 2013]. In canine melanoma as well, the strategy of xenogeneic vaccination, in particular with a plasmid encoding for the human form of the antigen CSPG4, has revealed to be effective for obtaining longer survival times in patients, who developed antibodies directed against both the human and canine forms of the target antigen [Riccardo 2014]. Therefore, xenogeneic vaccination represents a therapeutic anti-tumour strategy that may be explored against various tumour-associated antigens both in humans and in dogs.

SUMMARY

In some embodiments, an amino acid sequence of the antigen telomerase, where the amino acid sequence being selected from the group consisting of: an amino acid consensus sequence of the antigen telomerase comprising of sequence SEQ ID NO:1; a chimeric amino acid sequence of dog and human telomerase comprising of sequence SEQ ID NO:2, or a chimeric amino acid sequence of human and dog telomerase comprising of sequence SEQ ID NO:3, preferably an amino acid consensus sequence of the antigen telomerase comprising or consisting of sequence SEQ ID NO:1. In some embodiments, the amino acid sequence also includes one or more leader sequences. In some embodiments, the amino acid sequence also includes one or more immunomodulating amino acid sequences.

In some embodiments, a nucleotide sequence encodes the amino acid sequence of the antigen telomerase consisting of: an amino acid consensus sequence of the antigen telomerase comprising of sequence SEQ ID NO:1; a chimeric amino acid sequence of dog and human telomerase comprising of sequence SEQ ID NO:2, or a chimeric amino acid sequence of human and dog telomerase comprising of sequence SEQ ID NO:3, preferably an amino acid consensus sequence of the antigen telomerase comprising of sequence SEQ ID NO: 1.

In some embodiments, the nucleotide sequence is selected from the group consisting of a nucleotide sequence comprising sequence SEQ ID NO:4, or a nucleotide sequence comprising a sequence having a sequence identity of at least 80% with respect to SEQ ID NO:4, a nucleotide sequence comprising SEQ ID NO: 5 or a nucleotide sequence comprising SEQ ID NO:6. In some embodiments, the nucleic acid sequence comprises the nucleotide sequence SEQ ID NO:4, or a nucleotide sequence comprising a sequence having a sequence identity of at least 80% with respect to SEQ ID NO:4, and a nucleotide sequence encoding the profilin-like protein of *Toxoplasma gondii*. In some embodiments, the nucleotide sequence encoding the profilin-like protein of *Toxoplasma gondii* comprises SEQ ID NO:31.

In some embodiments, a nucleotide sequence encodes the amino acid sequence of the antigen telomerase consisting of: an amino acid consensus sequence of the antigen telomerase comprising of sequence SEQ ID NO:1; a chimeric amino acid sequence of dog and human telomerase comprising of sequence SEQ ID NO:2, or a chimeric amino acid sequence of human and dog telomerase comprising of sequence SEQ ID NO:3, preferably an amino acid consensus sequence of the antigen telomerase comprising or consisting of sequence SEQ ID NO:1; and one or more leader sequences. The one or more leader sequence is a secretion leader sequence of a protein selected from the group consisting of tissue plasminogen activator (TPA), IgK, growth hormone, serum albumin, and alkaline phosphatase.

In some embodiments, a nucleotide sequence encodes the amino acid sequence of the antigen telomerase consisting of: an amino acid consensus sequence of the antigen telomerase comprising of sequence SEQ ID NO:1; a chimeric amino acid sequence of dog and human telomerase comprising of sequence SEQ ID NO:2, or a chimeric amino acid sequence of human and dog telomerase comprising of sequence SEQ ID NO:3, preferably an amino acid consensus sequence of the antigen telomerase comprising or consisting of sequence SEQ ID NO:1; and one or more one or more immunomodulating amino acid sequences. The one or more immunomodulating amino acid sequences are selected from the group consisting of the fragment crystallisable (Fc) region, profilin-like protein of *Toxoplasma gondii* (PFTG) or a functional fragment derived therefrom, the B subunit of the heat-labile toxin of *Escherichia coli* (LTB) and the tetanus toxin (TT).

In some embodiments, an expression vector comprises the nucleotide sequence. In some embodiments, the expression vector is selected from the group consisting of a plasmid, an RNA, a replicating RNA, amplicons obtained by PCR, and a viral vector.

In some embodiments, a pharmaceutical composition comprises of the amino acid sequence in combination with one or more excipients and/or adjuvants.

In some embodiments, a method of vaccinating a subject against telomerase-expressing tumors or treating a subject having a telomerase-expressing tumors, comprise administering the amino acid sequence to the subject.

In some embodiments, a DNA or RNA-based vaccine comprises a nucleotide sequence. The nucleotide sequence encodes the amino acid sequence of the antigen telomerase consisting of: an amino acid consensus sequence of the antigen telomerase comprising of sequence SEQ ID NO:1; a chimeric amino acid sequence of dog and human telomerase comprising of sequence SEQ ID NO: 2, or a chimeric amino acid sequence of human and dog telomerase comprising of sequence SEQ ID NO:3, preferably an amino acid consensus sequence of the antigen telomerase comprising of sequence SEQ ID NO:1.

In some embodiments, a method of vaccinating a subject against telomerase-expressing tumors or treating a subject having a telomerase-expressing tumors, comprise administering a vaccine. The vaccine is a DNA or RNA-based vaccine which comprises a nucleotide sequence encoding the amino acid sequence of the antigen telomerase consisting of: an amino acid consensus sequence of the acid sequence of dog and human telomerase comprising of sequence SEQ ID NO: 2, or a chimeric amino acid sequence of human and dog telomerase comprising of sequence SEQ ID NO:3, preferably an amino acid consensus sequence of the antigen telomerase comprising of sequence SEQ ID NO:1.

In some embodiments, a kit for the prevention and treatment of telomerase-expressing tumours, the kit comprising a) a pharmaceutical composition, and b) a device for in vivo gene transduction.

In some embodiments, a pharmaceutical composition comprises a nucleotide sequence encoding the amino acid sequence of the antigen telomerase consisting of: an amino acid consensus sequence of the antigen telomerase comprising of sequence SEQ ID NO:1; a chimeric amino acid sequence of dog and human telomerase comprising of sequence SEQ ID NO:2, or a chimeric amino acid sequence of human and dog telomerase comprising of sequence SEQ ID NO:3, preferably an amino acid consensus sequence of the antigen telomerase comprising of sequence SEQ ID NO:1 in combination with one or more excipients and/or adjuvants.

In some embodiments, a protein-based vaccine comprising an amino acid sequence of the antigen telomerase, where the amino acid sequence being selected from the group consisting of: an amino acid consensus sequence of the antigen telomerase comprising of sequence SEQ ID NO:1; a chimeric amino acid sequence of dog and human telomerase comprising of sequence SEQ ID NO: 2, or a chimeric amino acid sequence of human and dog telomerase comprising of sequence SEQ ID NO:3, preferably an amino acid consensus sequence of the antigen telomerase comprising or consisting of sequence SEQ ID NO: 1.

The present invention fits into this context, as it aims to provide a chimeric vaccine capable of increasing the cellular and antibody immune response against telomerase.

According to the present invention, a telomerase consensus between humans and dogs and a nucleotide sequence encoding for said telomerase consensus have now been devised to be advantageously used in the preventive and therapeutic vaccination against telomerase-expressing tumours.

For this purpose, three different approaches have been developed, all of them aimed at creating a chimeric fusion protein from human and dog telomerase. According to the first approach, a chimeric canine-human sequence (CaHu) containing a codon-optimised sequence first of dTERT and then of hTERT has been created, followed by the profilin-like protein of *Toxoplasma gondii* (PFTG), a protein known for strengthening the immune response [Yarovinsky 2005]. In the second approach, a chimeric human-canine (CaHu) containing a codon-optimised sequence first of hTERT and then of dTERT, followed by PFTG, was created. Finally, in the third approach, a consensus sequence between dTERT and hTERT (conTRT) followed by PFTG was created through a bioinformatic approach.

According to the present invention, it was surprisingly found in a murine model that the genetic vaccine directed against telomerase and encoding for conTRT is more immunogenic and cross-reactive compared to the chimeric sequences CaHu and HuCa. Furthermore, according to the present invention, an antitumour effect was observed in a murine tumour model of colorectal cancer expressing hTert thanks to a preventive treatment with the conTRT vaccine. Both in healthy beagles and in dogs affected by lymphoma, an immunogenicity of the conTRT vaccine against both hTERT and dTERT was observed. The experimental results obtained using a DNA vaccine according to the present invention make it plausible also to assume an anti-tumour effectiveness of administering the protein sequences encoded by said DNA vaccine.

It is therefore a specific object of the present invention an amino acid sequence of the antigen telomerase, said amino acid sequence being selected from among:

an amino acid consensus sequence of the antigen telomerase comprising or consisting of sequence SEQ ID NO:1;

a chimeric amino acid sequence of dog and human telomerase comprising or consisting of sequence SEQ ID NO:2, or a chimeric amino acid sequence of human and dog telomerase comprising or consisting of sequence SEQ ID NO:3, preferably an amino acid consensus sequence of the antigen telomerase comprising or consisting of sequence SEQ ID NO:1.

The amino acid sequence according to the present invention can further comprise one or more leader sequences such as, for example, the secretion leader sequence of the tissue plasminogen activator (TPA), of IgK, of growth hormone, of serum albumin or of alkaline phosphatase, preferably of the tissue plasminogen activator.

Furthermore, the amino acid sequence according to the present invention can further comprise one or more immunomodulating amino acid sequences, such as, for example, the fragment crystallisable (Fc) region, profilin-like protein of *Toxoplasma gondii* (PFTG) or a functional fragment derived therefrom, the B subunit of the heat-labile toxin of *Escherichia coli* (LTB) or the tetanus toxin (TT), preferably profilin-like protein of *Toxoplasma gondii*.

The present invention further relates to a nucleotide sequence encoding for the amino acid sequence as defined above.

The nucleotide sequence according to the present invention can be selected from a nucleotide sequence comprising or consisting of sequence SEQ ID NO:4, or of a sequence having a sequence identity of at least 80% with respect to SEQ ID NO: 4, of sequence SEQ ID NO:5 or of sequence SEQ ID NO:6, preferably a nucleotide sequence comprising or consisting of sequence SEQ ID NO:4. For example, said sequence having a sequence identity of at least 80% with respect to SEQ ID NO:4 can have a sequence identity of at least 80%, 81%, 82%, 83%, 84%, 85%, 86%, 87%, 88%, 89%, 90%, 91%, 92%, 93%, 94%, 95%, 96%, 97%, 98%, 99%.

As mentioned above, the nucleotide sequence can further comprise a nucleotide sequence encoding for one or more leader sequences such as, for example, the secretion leader sequence of the tissue plasminogen activator (TPA), of IgK, of growth hormone, of serum albumin or of alkaline phosphatase, preferably of the tissue plasminogen activator. The nucleotide sequence can further comprise a nucleotide sequence encoding for one or more immunomodulating amino acid sequences, that is, sequences capable of strengthening the activation of the immune system, such as, for example, the fragment crystallisable (Fc) region, profilin-like protein of *Toxoplasma gondii* (PFTG) or a functional fragment derived therefrom, the B subunit of the heat-labile toxin of *Escherichia coli* (LTB) or the tetanus toxin (TT), preferably profilin-like protein of *Toxoplasma gondii*.

According to a preferred embodiment of the present invention, said nucleotide sequence comprises the nucleotide sequence SEQ ID NO:4, or a sequence having a sequence identity of at least 80% with respect to SEQ ID NO:4, and the nucleotide sequence encoding the profilin-like protein of *Toxoplasma gondii*. In particular, said nucleotide sequence encoding the profilin-like protein of *Toxoplasma gondii* can comprise or consist of the sequence TCTAGAAGCGACTGGGACCCCGTGGT-GAAGGAATGGCTGGTGGACACCG GCTACTGCTGTGCCGGCGGAATCGC-CAACGCCGAGGATGGCGTGGTGTT CGCCGCTGCAGCCGACGATGACGACGGCTG-GAGCAAGCTGTACAAGGA CGACCACGAG-GAGGACAC-CATCGGCGAGGACGGCAACGCCTGTGGCAA GGTGTCCATCAACGAGGCCAGCACCAT-CAAGGCCGCCGTGGACGACGG CAGCGCCCC-CAACGGAGTGTGGATCGGCGGCCAGAAATA-CAAGGTTGTG AGGCCCGAGAAGGGCTTCGAGTA-CAACGACTGTACCTTCGACATCACCA TGTGTGCCAGAAGCAAAGGCGGAGCCCACCTGAT-CAAGACCCCCAACGG CAGCATCGT-GATCGCCCTGTACGACGAG-GAGAAGGAGCAGGACAAGGG GGCTACTGATGA (SEQ ID NO:31), wherein the first six nucleotides of sequence TCTAGA encode for a cloning site of sequence SR, whereas the last six nucleotides of sequence TGATGA encode for two consecutive stop codons. The present invention further relates to an expression vector comprising the nucleotide sequence as defined above.

The expression vector can be selected from the group consisting of a plasmid, for example bacterial plasmids, an RNA, a replicating RNA, amplicons obtained by PCR, a viral vector such as, for example, adenovirus, poxvirus, vaccinia virus, fowlpox, herpes virus, adeno-associated virus (AAV), alphavirus, lentivirus, lambda phage, lymphocytic choriomeningitis virus, *Listeria* sp, and *Salmonella* sp.

The present invention further relates to a pharmaceutical composition comprising an amino acid sequence as defined above, a nucleotide sequence as defined above or an expression vector as defined above, in combination with one or more pharmaceutically acceptable excipients and/or adjuvants.

Furthermore, the present invention relates to an amino acid sequence as defined above, a nucleotide sequence as defined above, an expression vector as defined above or a pharmaceutical composition as defined above, for use in the medical field.

It is a further object of the present invention an amino acid sequence as defined above, a nucleotide sequence as defined above, an expression vector as defined above or a pharmaceutical composition as defined above, for use in the prevention and treatment of telomerase-expressing tumours, such as, for example, lymphomas, hemangiosarcoma and prostate cancer.

According to the present invention, the amino acid sequence as defined above, the nucleotide sequence as defined above, the expression vector as defined above or the pharmaceutical composition as defined above can be advantageously employed as a DNA, RNA or protein-based vaccine. When the vaccine is a DNA or RNA vaccine, said vaccine can be administered by electroporation, preferably under the following conditions: 8 pulses of 20 msec, each at 110V, 8 Hz, with an interval of 120 msec between each of them.

According to the present invention, the above-described use can be a use either in the human sector or in the veterinary sector, for example in man or in dogs.

The present invention further relates to a kit for the prevention and treatment of telomerase-expressing tumours, said kit comprising or consisting of: a) nucleotide sequence as defined above, expression vector as defined above or pharmaceutical composition as defined above comprising said nucleotide sequence or said vector, and b) a device for in vivo gene transduction, such as, for example, a device for administration by electroporation.

The present invention will now be described, by an illustrative but non-limiting way, according to a preferred embodiment thereof, with particular reference to the examples and the figures in the appended drawings, wherein:

BRIEF DESCRIPTION OF THE DRAWINGS

FIG. 1 shows the homology between the amino acid sequences of hTERT, HuCa, dTERT, CaHu and conTRT: A) amino acids 1-500; B) amino acids 501-1000; C) amino acids 1001-1141.

FIG. 2 shows the number of splenocytes (expressed as spot-forming cells, SFC per million) secreting IFN determined by means of the ELISpot technique, after 16 hours of stimulation with pools A, B, C and D of 15-mer peptides and overlapping by 11 amino acid residues both of the hTERT protein and of the dTERT protein, isolated from wild-type mice vaccinated, by electroporation, with the hTERT, dTERT, CaHu, HuCa and conTRT vaccines. The white circles indicate the number of SFC per single mouse, the black circle indicates the geometric mean of SFC of the group.

FIG. 5 shows the number of PBMCs isolated from dogs with lymphoma and secreting IFNγ determined by means of the ELISpot technique, after 16 hours of stimulation with pools A, B, C and D of 15-mer peptides and overlapping by 11 amino acid residues both of the hTERT protein and of the dTERT protein. The graph shows the specific immune response for dog and human telomerase measured in the group of dogs vaccinated with 5 mg of DNA 4 weeks after the last vaccination.

DETAILED DESCRIPTION

Figure 3:
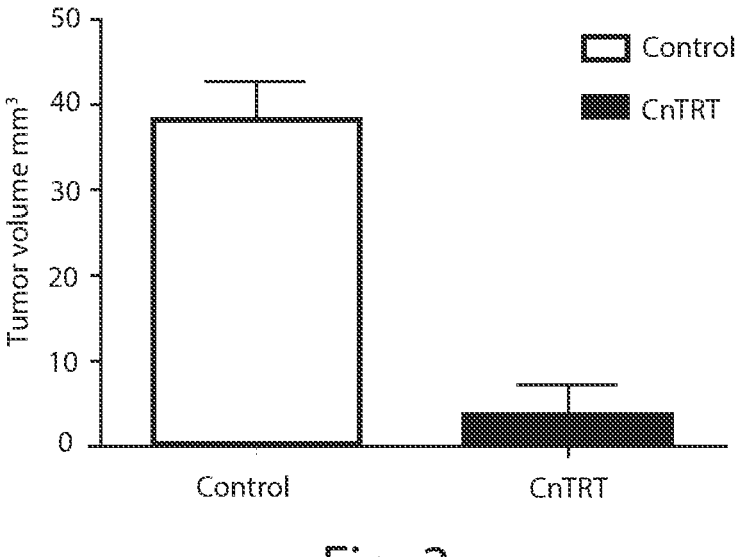
FIG. 3 shows the tumour volume of a group of Balb/c mice vaccinated with the conTRT vaccine prior to the inoculation of tumour cells (prophylactic setting) compared to the tumour volume measured in the group of unvaccinated control mice.

Example 1. Design of the Consensus Sequence of the Antigen Telomerase and of the Nucleotide Sequence Encoding Said Consensus Sequence and In Vivo Study on Effectiveness in the Preventive and Therapeutic Vaccination for Telomerase-Expressing Tumours Design of the optimised nucleotide sequence of dTERT and hTERT The optimised cDNA encoding for the hTERT sequence (SEQ ID NO:7) is:

```
atgccgcgcgctccccgctgccgagccgtgcgctccctgctgcgcagccactaccgcgaggtgct gccgctggccacgttcgtgcggcgcctggggccccagggctggcggctggtgcagcgcggggacccggc ggctttccgcgcgctggtggcccagtgcctggtgtgcgtgccctgggacgcacggccgcccccgccgccc cctccttccgccaggtgtcctgcctgaaggagctggtggcccgagtgctgcagaggctgtgcgagcgcggc gcgaagaacgtgctggccttcggcttcgcgctgctggacggggcccgcggggcccccccgaggccttca ccaccagcgtgcgcagctacctgcccaacacggtgaccgacgcactgcggggggagcggggcgtggggg ctgctgctgcgccgcgtgggcgacgacgtgctggttcacctgctggcacgctgcgcgctctttgtgctggtggc tcccagctgcgcctaccaggtgtgcgggccgccgctgtaccagctcggcgctgccactcaggcccggcccc cgccacacgctagtggaccccgaaggcgtctgggatgcgaacgggcctggaaccatagcgtcaggag gccggggtcccccttgggcctgccagccccgggtgcgaggaggcgcggggggcagtgccagccgaagtct gccgttgcccaagaggcccaggcgtggcgctgccccctgagccggagcggacgcccgttgggcaggggtc ctgggcccacccgggcaggacgcgtggaccgagtgaccgtggtttctgtgtggtgtcacctgccagacccg ccgaagaagccacctctttggagggtgcgctctctggcacgcgccactcccacccatccgtgggccgccag caccacgcgggccccccatccacatcgcggccaccacgtccctgggacacgccttgtccccggtgtacg ccgagaccaagcacttcctctactcctcaggcgacaaggagcagctgcggccctccttcctactcagctctct gaggcccagcctgactggcgctcggaggctcgtggagaccatctttctgggttccaggccctggatgccagg gactccccgcaggttgccccgcctgccccagcgctactggcaaatgcggcccctgtttctggagctgcttggg aaccacgcgcagtgcccctacggggtgctcctcaagacgcactgcccgctgcgagctgcggtcaccccag cagccggtgtctgtgcccgggagaagcccagggctctgtggcggcccccgaggaggaggacacagac ccccgtcgcctggtgcagctgctccgccagcacagcagcccctggcaggtgtacggcttcgtgcgggcctg cctgcgccggctggtgcccccaggcctctggggctccaggcacaacgaacgccgcttcctcaggaacacc aagaagttcatctccctggggaagcatgccaagctctcgctgcaggagctgacgtggaagatgagcgtgcg ggactgcgcttggctgcgcaggagcccaggggttggctgtgttccggccgcagagcaccgtctgcgtgagg agatcctggccaagttcctgcactggctgatgagtgtgtacgtcgtcgagctgctcaggtctttctttttatgtcacg gagaccacgtttcaaaagaacaggctcttttttctaccggaagagtgtctggagcaagttgcaaagcattgga atcagacagcacttgaagagggtgcagctgcgggagctgtcggaagcagaggtcaggcagcatcggga agccaggcccgccctgctgacgtccagactccgcttcatccccaagcctgacgggctgcggccgattgtga
```

-continued

```
acatggactacgtcgtgggagccagaacgttccgcagagaaaagagggccgagcgtctcacctcgaggg tgaaggcactgttcagcgtgctcaactacgagcgggcgcggcgccccggcctcctgggcgcctctgtgctg ggcctggacgatatccacagggcctggcgcaccttcgtgctgcgtgtgcgggcccaggacccgccgcctg agctgtactttgtcaaggtggatgtgacgggcgcgtacgacaccatcccccaggacaggctcacggaggtc atcgccagcatcatcaaaccccagaacacgtactgcgtgcgtcggtatgccgtggtccagaaggccgccc atgggcacgtccgcaaggccttcaagagccacgtctctaccttgacagacctccagccgtacatgcgacag ttcgtggctcacctgcaggagaccagcccgctgagggatgccgtcgtcatcgagcagagctcctccctgaat gaggccagcagtggcctcttcgacgtcttcctacgcttcatgtgccaccacgccgtgcgcatcaggggcaag tcctacgtccagtgccaggggatcccgcagggctccatcctctccacgctgctctgcagcctgtgctacggcg acatggagaacaagctgtttgcggggattcggcgggacgggctgctcctgcgtttggtggatgatttcttgttgg tgacacctcacctcacccacgcgaaaaccttcctcaggaccctggtccgaggtgtccctgagtatggctgcgt ggtgaacttgcggaagacagtggtgaacttccctgtagaagacgaggccctgggtggcacggcttttgttca gatgccggcccacggcctattcccctggtgcggcctgctgctggataccoggaccctggaggtgcagagcg actactccagctatgcccggacctccatcagagccagtctcaccttcaaccgcggcttcaaggctgggagg aacatgcgtcgcaaactctttggggtcttgcggctgaagtgtcacagcctgtttctggatttgcaggtgaacagc ctccagacggtgtgcaccaacatctacaagatcctcctgctgcaggcgtacaggtttcacgcatgtgtgctgc agctcccatttcatcagcaagtttggaagaaccccacattttcctgcgcgtcatctctgacacggcctccctctg ctactccatcctgaaagccaagaacgcagggatgtcgctgggggccaagggcgccgccggccctctgcc ctccgaggccgtgcagtggctgtgccaccaagcattcctgctcaagctgactcgacaccgtgtcacctacgt gccactcctggggtcactcaggacagcccagacgcagctgagtcggaagctcccggggacgacgctgac tgccctggaggccgcagccaacccggcactgccctcagacttcaagaccatcctggactga
```

The optimised cDNA encoding for the dTERT sequence (SEQ ID NO:8) is:

```
atggacgccatgaagaggggcctgtgctgcgtgctgctgctgtgcggagccgtgttcgtgagccccc agcgagatccccagagcccccagatgtagggccgtgagggccctgctgaggggcagatacagagaggt gctgcccctggccaccttcctgagaaggctgggccctcctggcagactgctggtccgcagaggcgatcctgc cgcctttagagccctggtggcccagtgcctggtctgtgtgcccttggggagccagacctcctcctgccgcccctt gcttcaggcaggtgtcctgcctgaaagaactggtggccagggtggtgcagagactgtgcgagaggggcgc cagaaacgtgctggccttcggctttgccctgctggatggcgctagaggcggccctcctgtggccttcaccacc tccgtgcggagctacctgcccaacaccgtgaccgagaccctgagaggaagcggagcctggggcctgctg ctgagaagagtgggcgacgacgtgctgacccacctgctggcagatgcgccctgtacctgctggtcgcccc tagctgtgcctaccaggtctgcggccctcccctgtatgacctgtgcgcccctgcctctctgcctctgcctgcccct ggactgcctggcctgccagggctgcctggactgggagctggcgctggcgcctctgccgacctgagacccca ccagacaggcccagaacagcggcgccagaagaagaagaggcagccccggaagcggcgtgcctctgg ccaagaggcctcggagaagcgtggcctctgagcccgaaagaggcgcccacagaagcttccccagagcc cagcagcctcctgtgtctgaggccctgccgtgacacctgccgtggccgcctctcctgctgcttcttgggaggg cggacctcctggaaccagacccaccacccccgcctggcacccttatcctggccctcagggcgtgcctcacg atcctgcccaccccgagaccaagcggttcctgtactgcagcggcggcagagagaggctgaggcccagctt cctgctgtctgccctgcctcctaccctgagcggagcccggaaactggtggagaccatcttcctgggcagcgct cctcagaagcctggcgccgctcggagaatgcggaggctgcccgccagatactggcggatgcggcccctgt
```

-continued

```
tccaggaactgctgggcaaccacgccagatgcccctacagggccctgctgaggacccactgccctctgag ggccatggccgccaaagagggcagcggcaaccaggcccacagaggcgtgggcatctgcccccctggaa agacccgtggccgctccccaggaacagaccgacagcaccaggctggtgcagctgctgagacagcacag cagccctggcaggtgtacgccttcctgagggcctgcctgtgttggctggtgcctaccggcctgtggggcagc aggcacaaccagaggcggtttctgaggaacgtgaagaagttcatcagcctgggcaagcacgccaagctgt ccctgcaggaactgacctggaagatgaaagtgcgggactgcacctggctgcacggcaatcctggcgcctg ttgtgtgcctgccgccgagcacaggcggagggaagagatcctggcccggttcctggtgctggtcgatggcc acatctacgtggtgaagctgctgcggagcttcttctacgtgaccgagaccaccttccagaaaaataggctgtt cttctaccggaagagcgtgtggagccagctgcagagcatcggcatcaggcagctgttcaacagcgtgcac ctgagagagctgtccgaggccgaagtgaggcggcacagagaggccagacccgccctgctgaccagca ggctgagattcctgcccaagcccagcggcctgaggcccatcgtgaacatggactacatcatgggcgccag gaccttccacagggacaagaaggtgcagcacctgaccagccagctgaaaaccctgttcagcgtgctgaac tacgagagggccagaaggcctagcctgctgggcgccagcatgctgggcatggacgacatccacagggc ctggcggaccttcgtgctgaggatcagggcccagaaccctgcccccagctgtacttcgtgaaggtggccat caccggcgcctacgacgccctgcctcaggacagactggtggaggtgatcgccaacgtgatcaggcccca ggaaagcacctactgcgtcaggcactacgccgtggtgcagagaaccgccaggggccacgtgaggaagg ccttcaagaggcacgtgagcaccttcgccgacctgcagccctacatgaggcagttcgtggagaggctgcag gagaccagcctgctgagggatgccgtggtgatcgagcagagcagcagcctgaacgaggccggcagctc cctgttccacctgtttctgaggctggtgcacaaccacgtggtgcggatcggcggcaagagctacatccagtgc cagggcgtgcctcagggcagcatcctgagcaccctgctgtgcagcctgtgctacggcgacatggaaaggc ggctgttccctggcatcgagcaggacggcgtgctgctgagactggtggacgacttcctgctggtgacccctca tctgacccaggcccaggccttcctgagaaccctggtgaagggcgtgcccgagtacggctgcagggccaac ctgcagaaaaccgccgtgaacttccctgtggaggacggcgctctgggatctgctgcccctctgcagctgcct gcccactgcctgttcccttggtgcggcctgctgctggacaccaggaccctggaagtgagctgcgactacagc agctacgcccacaccagcatcagggccagcctgaccttcagccagggcgccaagcccggcaggaacat gcggaggaagctgctggccgtgctgaggctgaagtgctgcgccctgttcctggacctgcaggtcaacggca tccacaccgtgtacatgaacgtgtacaaaatcttcctgctgcaggcctacaggttccacgcctgcgctgctgca gctgcccttcaaccagcccgtgaggaagaaccccagcttcttcctgagggtgatcgccgacaccgccagct gctgctacagcctgctgaaggccagaaatgccggcctgtctctgggagccaagggcgccagcggcctgttt cctagcgaggccgccagatggctgtgcctgcacgcctttctgctgaagctggcccaccacagcggcaccta cagatgcctgctgggagccctgcaggccgccaaagcccacctgagcaggcagctgcctagaggaacact ggccgccctggaagccgccgctgaccctagcctgaccgccgacttcaagaccatcctggac
```

Design of the Optimised Nucleotide Sequence of CaHu and HuCa.

The design of the optimised cDNA encoding for the chimeric CaHu sequence was created on the basis of the dTERT and hTERT sequences, both submitted to the NCBI database with accession numbers NM_001031630.1 and NM_198253.3, respectively.

The optimised cDNA encoding for the CaHu sequence (SEQ ID NO:5) is:

```
atgggctggtcctgtattattctgtttctggtcgccaccgctaccggagtccatagtcctagagcaccccgctgtc gcgccgtgagggccctgctgagaggcaggtaccgcgaggtgctgccactggctacctttctgcggagactg
```

-continued

```
ggaccacctggcaggctgctggtgaggcgaggcgaccctgcagctttccgcgccctggtggctcagtgcct ggtgtgcgtgccttggggagcaaggccaccacctgcagcaccatgctttcgacaggtgagctgtctgaagg agctggtcgcacgagtggtccagcgactgtgcgaaaggggcgctcgcaacgtgctggcattcggctttgcc ctgctggatggagctcgaggaggaccaccagtggccttcaccaccagcgtgcggagctacctgcccaata ctgtgaccgagacactgaggggatccggagcatggggactgctgctgcgacgagtgggggacgatgtcct gacacacctgctggcacgctgcgccctgtatctgctggtggctccctcatgcgcataccaggtctgtggccctc cactgtatgacctgtgcgcacctgccagcctgcccctgcctgccccagggctgcctggactgccaggactgc caggactgggagctggagcaggggcctcagctgatctgcgacctacccggcaggctcagaacagcgga gcaagaaggcgccgaggaagtccaggatcaggagtgcctctggcaaagaggccacggagaagcgtcg catccgagccagaacgaggagctcaccggagcttccctagggcacagcagccacctgtgagtgaggcac ctgcagtgactccagcagtcgctgcaagtcctgcagcttcatgggaaggaggaccaccaggaacccgacc tactaccccagcttggcatccataccctggaccacagggagtgccacacgaccctgcccatccagagacc aagcggtttctgtattgcagcgggggacgagaacggctgagaccaagcttcctgctgtccgccctgcctcca acactgagtggggctagaaaactggtggagactatctttctgggatcagctccacagaagcctggagcagc aaggcgaatgcgacggctgcctgccaggtactggaggatgcgcccactgttccaggagctgctgggaaac cacgctcgatgcccctatcgagcactgctgcggacacattgtcctctgcgggcaatggctgcaaaggaagg gagtggaaatcaggcacaccgaggagtgggaatctgcccctggagagacctgtcgcagctccacagga acagaccgacagcacacgactggtgcagctgctgcgccagcatagctccccatggcaggtgtacgcctttc tgagagcttgcctgtgctggctggtgccaaccggactgtggggggtccaggcacaaccagagaaggtttctgc gcaatgtgaagaaattcatctccctgggcaagcatgccaaactgtctctgcaggagctgacctggaagatga aagtgaggggactgtacatggctgcacggaaacccaggagcttgctgcgtgcctgcagcagaacatcgccg acgggaggaaatcctggccagatttctggtgctggtcgatggacacatctacgtggtcaaactgctgaggtct ttctttatgtgaccgagacaactttccagaagaataggctgttcttttatcgcaagagcgtgtggagtaaactgc agtctatcggcattagacagcacctgaaaagagtgcagctgagggagctgagtgaggccgaagtcagac agcatagggaagctcgccctgcactgctgacaagccgactgcggttcatccccaagcctgacgggctgcg cccaattgtgaacatggattacgtggtcggagcacggacctttagaagggagaaacgagccgaacggctg acatcaagagtgaaggctctgttcagcgtcctgaattatgagagggcacgccgacccggactgctgggagc ctctgtgctggggctggacgacatccacagagcttggaggacctttgtgctgagagtcagggcacaggacc cccctccagagctgtacttcgtgaaggtcgcaatcaccggagcctatgacacaattccacaggatcgcctga ctgaagtgattgccagcatcatcaagcccagaatacctactgcgtgcggagatatgcagtggtccagaag gctgcacacggccatgtgcggaaggcctttaaatcacacgtcagcactctgaccgatctgcagccttacatg cgccagttcgtggctcatctgcaggagacttctccactgcgggacgcagtggtcatcgagcagtctagttcact gaacgaagctagctccgggctgttcgacgtgttcctgaggttcatgtgccaccatgccgtgcgcattcgagga aaatcctacgtccagtgtcagggaatcccacagggctccattctgtctaccctgctgtgctctctgtgctatggc gacatggagaataagctgtttgcaggcatcaggcgagatggactgctgctgagactggtggacgattttctgc tggtcaccccccacctgacacatgccaaaactttcctgcgcaccctggtgcgaggagtccctgaatacggct gcgtggtcaacctgaggaagacagtggtcaatttcccagtggaggacgaagccctgggaggaactgctttt gtccagatgccagcacacggactgttcccatggtgtggactgctgctggacacacgcactctggaggtgca gagcgattactctagttatgcccggacatctatcagagctagtctgacttttaaccggggggttcaaggccggaa gaaatatgcgacggaaactgtttggcgtgctgcgggctgaagtgccatagtctgttcctggacctgcaggtgaa ctcactgcagactgtctgtaccaatatctacaaaattctgctgctgcaggcatatagatttcacgcctgcgtgct
```

-continued

```
gcagctgccattccatcagcaggtctggaagaaccccacttttttctgagagtgatcagcgataccgctagc ctgtgctactccattctgaaggccaaaaatgctggaatgtccctgggagcaaaaggagcagctggaccact gccatctgaggctgtgcagtggctgtgccaccaggcattcctgctgaagctgactcggcatagagtgacctat gtcccactgctgggaagcctgcggacagcccagactcagctgtccagaaagctgccaggaaccacactg accgccctggaagcagccgctaacccagctctgcccagcgactttaaaacaatcctggat
```

The following CaHu amino acid sequence (SEQ ID NO:2) was obtained from the fusion (FIGS. 1-3):

```
MPRAPRCRAVRALLRGRYREVLPLATFLRRLGPPGRLLVRRGDPAAFRA

LVAQCLVCVPWGARPPPAAPCFRQVSCLKELVARVVQRLCERGARNVLA

FGFALLDGARGGPPVAFTTSVRSYLPNTVTETLRGSGAWGLLLRRVGDD

VLTHLLARCALYLLVAPSCAYQVCGPPLYDLCAPASLPLPAPGLPGLPG

LPGLGAGAGASADLRPTRQAQNSGARRRRGSPGSGVPLAKRPRRSVASE

PERGAHRSFPRAQQPPVSEAPAVTPAVAASPAASWEGGPPGTRPTTPAW

HPYPGPQGVPHDPAHPETKRFLYCSGGRERLRPSFLLSALPPTLSGARK

LVETIFLGSAPQKPGAARRMRRLPARYWRMRPLFQELLGNHARCPYRAL

LRTHCPLRAMAAKEGSGNQAHRGVGICPLERPVAAPQEQTDSTRLVQLL

RQHSSPWQVYAFLRACLCWLVPTGLWGSRHNQRRFLRNVKKFISLGKHA

KLSLQELTWKMKVRDCTWLHGNPGACCVPAAEHRRREEILARFLVLVDG

HIYVVKLLRSFFYVTETTFQKNRLFFYRKSVWSQLQSIGIRQLFNSVHL

RELSEAEVRRHREARPALLTSRLRFLPKPSGLRPIVNMDYIMGARTFHR
```

-continued

```
DKKVQHLTSQLKTLFSVLNYERARRPSLLGASMLGMDDIHRAWRTFVLR

IRAQNPAPQLYFVKVAITGAYDTIPQDRLTEVIASIIKPQNTYCVRRYA

VVQKAAHGHVRKAFKSHVSTLTDLQPYMRQFVAHLQETSPLRDAVVIEQ

SSSLNEASSGLFDVFLRFMCHHAVRIRGKSYVQCQGIPQGSILSTLLCS

LCYGDMENKLFAGIRRDGLLLRLVDDFLLVTPHLTHAKTFLRTLVRGVP

EYGCVVNLRKTVVNFPVEDEALGGTAFVQMPAHGLFPWCGLLLDTRTLE

VQSDYSSYARTSIRASLTFNRGFKAGRNMRRKLFGVLRLKCHSLFLDLQ

VNSLQTVCTNIYKILLLQAYRFHACVLQLPFHQQVWKNPTFFLRVISDT

ASLCYSILKAKNAGMSLGAKGAAGPLPSEAVQWLCHQAFLLKLTRHRVT

YVPLLGSLRTAQTQLSRKLPGTTLTALEAAANPALPSDFKTILD
```

The design of the optimised cDNA encoding for the chimeric HuCa sequence was created on the basis of the hTERT and dTERT sequences, both submitted to the NCBI database with accession numbers NM_198253.3 and NM_001031630.1, respectively.

The optimised cDNA encoding for the sequence HuCa (SEQ ID NO:6) is:

```
atgggatggtcttgtattattctgttcctggtcgccactgccaccggggtccacagccctagagcacctagatgt agagccgtgagaagtctgctgcgctcacactaccgagaggtgctgcctctggccacattcgtccggagactg ggaccacagggatggcgactggtgcagagaggcgatccagcagcttttagagctctggtcgcacagtgcct ggtgtgcgtgccatgggacgcacgaccacctccagcagcccctagcttccggcaggtgtcctgcctgaaag aactggtggcaagggtcctgcagcggctgtgcgagcgaggagctaagaacgtgctggcattcggatttgca ctgctggatggagcacgaggaggaccacctgaggcctttaccacaagcgtgcggtcctatctgcccaatac agtcactgacgctctgagaggcagcggagcatggggactgctgctgaggcgagtgggcgacgatgtgctg gtccacctgctggcacgatgcgctctgttcgtgctggtcgctccttcctgcgcataccaggtgtgcggaccacc actgtatcagctgggagctgcaacccaggcaagacctccaccacacgctagtggacctcgacggagactg ggatgtgaaagggcttggaaccattcagtgcgcgaggcaggagtcccactgggactgccagcacctggag caaggcgccgaggaggaagtgcctcacgaagcctgccactgccaaagcgaccacgaagaggagcag ctcctgaaccagagaggactcccgtgggacagggatcctgggcacacccaggaaggacccgggaccc tcagatagaggcttctgcgctggtcagccctgctaggccagcagaggaagccactagtctggagggcgcct gtcagggaccagacactctcatcccagtgtgggcaggcagcaccatgctgggcctccatccacatctcggc cccctagaccatgggatactccctgtccaccgtgtacgccgaaaccaaacatttcctgtatagctccggcga caaggagcagctgcgcccaagttttctgctgtctagtctgcgaccatcactgaccggagcaaggcgcctggt ggaaacaatcttcctgggaagcaggccctggatgcctggaactccacgacggctgccacgactgcctcag agatactggcagatgcgccctctgtttctggagctgctgggaaaccacgcacagtgcccatatggagtgctg
```

-continued ctgaaaacacattgtcccctgagggcagcagtgactcctgctgcaggcgtctgcgcacgagagaagccac agggaagcgtggcagctccagaggaagaggacaccgatcctagaaggctggtgcagctgctgaggcag cactcaagcccttggcaggtgtacggattcgtccgcgcatgtctgcgccgactggtgcctccaggactgtggg gaagccgccacaacgaacggagattcctgcgaaataccaagaagttcatctccctggggaagcatgcca aactgtctctgcaggagctgacatggaaaatgtcagtgagggactgcgcttggctgaggcgcagccctgga gtgggatgcgtgccagcagcagagcaccgactgcgagaagagattctggccaagttcctgcattggctgat gagcgtgtacgtggtcgaactgctgcgctccttcttttatgtcaccgagactacctttcagaagaacagactgtt cttttataggaaatcagtgtgggagccagctgcagagcatcggcattagacagctgttcaatagcgtgcacctg agggaactgtccgaagcagaggtccgacggcatagggaggctcgaccagcactgctgaccagccggct gaggtttctgcccaaacctagtggactgaggcccatcgtgaacatggattacattatgggcgccaggactttc caccgcgacaagaaagtgcagcatctgacctctcagctgaagacactgtttagtgtgctgaattatgagcga gcaagaaggccctctctgctgggagctagtatgctggggatggacgacatccaccgagcatggcggacctt cgtgctgcgcattcgagcccagaacccagctccccagctgtactttgtgaaggtcgccatcacaggagccta tgacgctctgccacaggataggctggtggaagtcatcgccaatgtgattcgaccacaggagtccacctactg cgtccggcattatgcagtggtccagagaacagccaggggccacgtgcgcaaggctttcaaacgacacgtg agcaccttcgccgacctgcagccatacatgcggcagtttgtggaaagactgcaggagaccagcctgctgcg agacgcagtggtcattgaacagtcctctagtctgaacgaggctggctcaagcctgttccacctgtttctgcgcct ggtgcacaatcatgtggtccggatcggggggaaagagttacattcagtgtcagggagtgccccagggctcca tcctgtctaccctgctgtgctccctgtgctatggcgatatggaacgccgactgttccccggaattgagcaggac ggcgtgctgctgcgactggtggacgatttcctgctggtgactcctcatctgacccaggcccaggcttttctgcgg acactggtgaaaggggtccccgaatacggatgcagagctaacctgcagaagactgcagtgaatttccctgt cgaggacggggccctgggatctgctgcacctctgcagctgccagctcactgcctgtttccatggtgtggcctg ctgctggatacccgacactggaggtgagctgtgactactcctcttatgcccatacaagcatcagagcttccct gactttctctcaggggggccaagcccggaagaaacatgcggagaaaactgctggcagtgctgaggctgaa gtgctgtgccctgtttctggatctgcaggtgaacggcatccacaccgtgtacatgaatgtctataaaaattttcctg ctgcaggcataccggtttcatgcctgcgtgctgcagctgcccttcaaccagcctgtcagaaagaatcctagctt ctttctgagagtgatcgcagacacagccagttgctgttattcactgctgaaagctagaaatgcaggactgtccc tgggagcaaagggagcttcaggactgttcccaagcgaagccgctaggtggctgtgcctgcacgcatttctgc tgaaactggcccaccatagcggaacttaccgatgtctgctgggcgctctgcaggcagccaaggcacatctgt cccgacagctgccacgagggaccctggctgcactggaggcagctgcagaccttctctgactgccgatttc aaaaccatcctggac The following HuCa amino acid sequence (SEQ ID NO:3) was obtained from the fusion (FIGS. 1-3):

PRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAF

GFALLDGARGGPPEAFTTSVRSYLPNTVTDALRGSGAWGLLLRRVGDDV

LVHLLARCALFVLVAPSCAYQVCGPPLYQLGAATQARPPPHASGPRRRL

GCERAWNHSVREAGVPLGLPAPGARRRGGSASRSLPLPKRPRRGAAPEP

ERTPVGQGSWAHPGRTRGPSDRGFCVVSPARPAEEATSLEGALSGTRHS

HPSVGRQHHAGPPSTSRPPRPWDTPCPPVYAETKHFLYSSGDKEQLRPS

FLLSSLRPSLTGARRLVETIFLGSRPWMPGTPRRLPRLPQRYWQMRPLF

LELLGNHAQCPYGVLLKTHCPLRAAVTPAAGVCAREKPQGSVAAPEEED

TDPRRLVQLLRQHSSPWQVYGFVRACLRRLVPPGLWGSRHNERRFLRNT

KKFISLGKHAKLSLQELTWKMSVRDCAWLRRSPGVGCVPAAEHRLREEI

LAKFLHWLMSVYVVELLRSFFYVTETTFQKNRLFFYRKSVWSKLQSIGI

RQHLKRVQLRELSEAEVRQHREARPALLTSRLRFIPKPDGLRPIVNMDY

VVGARTFRREKRAERLTSRVKALFSVLNYERARRPGLLGASVLGLDDIH

RAWRTFVLRVRAQDPPPELYFVKVAITGAYDALPQDRLVEVIANVIRPQ

-continued

ESTYCVRHYAVVQRTARGHVRKAFKRHVSTFADLQPYMRQFVERLQETS

LLRDAVVIEQSSSLNEAGSSLFHLFLRLVHNHVVRIGGKSYIQCQGVPQ

GSILSTLLCSLCYGDMERRLFPGIEQDGVLLRLVDDFLLVTPHLTQAQA

FLRTLVKGVPEYGCRANLQKTAVNFPVEDGALGSAAPLQLPAHCLFPWC

GLLLDTRTLEVSCDYSSYAHTSIRASLTFSQGAKPGRNMRRKLLAVLRL

KCCALFLDLQVNGIHTVYMNVYKIFLLQAYRFHACVLQLPFNQPVRKNP

SFFLRVIADTASCCYSLLKARNAGLSLGAKGASGLFPSEAARWLCLHAF

LLKLAHHSGTYRCLLGALQAAKAHLSRQLPRGTLAALEAAADPSLTADF

KTILD

The cDNA encoding for these sequences was optimised for codon usage. The cDNA optimisation consists in replacing the original codons with nucleotide triplets recognised by the tRNAs which are most frequent and efficient in the cells of the organism of interest. For this purpose use was made of an algorithm (GeneOptimizer, Thermofisher) that allows the cDNA of interest to be designed so as to increase the levels of expression in cells of the species in which it is desired to use the antigen (*Homo sapiens*). Furthermore, any undesired restriction sites or splicing sites generated in silico by this operation were removed. The DNA was synthesised by Invitrogen GeneArt (Germany) and cloned in the pTK1A-TPA vector.

Design of the conTRT Consensus Sequence.

The design of the optimised cDNA encoding for the consensus sequence conTRT was created on the basis of the dTERT and hTERT sequences by means of a bioinformatic method, by overlapping the sequences of the dog and human epitopes differing by a single amino acid and optimised for binding with human HLAs.

Table 1 shows a list of the dTERT and hTERT epitopes differing by a single amino acid and optimised for human HLAs.

TABLE 1

| Species | Starting Position | Epitope | Improved HLA Allele Binding |
|---------|-------------------|---------|------------------------------|
| Human | 4 | APRCRAVRS (SEQ ID NO: 9) | B7 |
| Dog | 4 | APRCRAVRA (SEQ ID NO: 10) | B7 |
| Human | 20 | EVLPLATFV (SEQ ID NO: 11) | B7 |
| Dog | 20 | EVLPLATFL (SEQ ID NO: 12) | B7 |
| Human | 554 | VELLRSFFY (SEQ ID NO: 13) | B*1503 |
| Dog | 544 | VKLLRSFFY (SEQ ID NO: 14) | B*1503 |
| Human | 616 | LLTSRLRFI (SEQ ID NO: 15) | A2 |
| Dog | 606 | LLTSRLRFL (SEQ ID NO: 16) | A2 |
| Human | 631 | RPIVNMDYV (SEQ ID NO: 17) | B51, B53 |
| Dog | 621 | RPIVNMDYI (SEQ ID NO: 18) | B51, B53 |
| Human | 659 | KALFSVLNY (SEQ ID NO: 19) | B58 |
| Dog | 649 | KTLFSVLNY (SEQ ID NO: 20) | B58 |
| Human | 682 | GLDDIHRAW (SEQ ID NO: 21) | A32 |
| Dog | 672 | GMDDIHRAW (SEQ ID NO: 22) | A32 |
| Human | 689 | AWRTFVLRV (SEQ ID NO: 23) | A24 |
| dog | 679 | AWRTFVLRI (SEQ ID NO: 24) | A24 |
| Human | 784 | SPLRDAVVI (SEQ ID NO: 25) | A68 |
| Dog | 775 | SLLRDAVVI (SEQ ID NO: 26) | A68 |

The optimised cDNA encoding for the conTRT sequence
(SEQ ID NO:4) is:

```
atgggatggtcatgtattattctgttcctggtcgctaccgcaaccggagtgcatagtccaagagcccc tagatgtcgagccgtgagggcactgctgcgcagccgataccgggaggtgctgcctctggctaccttcctgcg gagactgggaccacagggatggagactggtgaggcgaggggacccagcagcttttagggctctggtcgc acagtgcctggtgtgcgtgccatggggagcaagaccacctccagcagcccttcattcaggcaggtgagct gcctgaaagagctggtggctagggtcctgcagcggctgtgcgaacgaggagcaaagaacgtgctggcttt cgggtttgcactgctggacggagctagaggaggaccacctgtggccttcaccaccagcgtgcggagctatc tgcccaataccgtgacagatactctgcgaggatccggagcatggggactgctgctgcgacgggggggga cgatgtgctggtccacctgctggcacgatgcgctctgttcctgctggtggcccttcttgcgcttaccaggtctgt ggaccacccctgtatcagctgggcgccccaacaagtctgagacctccacccctgcttcaccaccaagaa ggcgcctgccaggactgagggcatggaaccatgccgtgcgcgacctgcgagtcactcgacagctgcaga atagcggagcacgacggagaaggggatccccaagctcctctctgccactgcctaagcgaccacgccgat ctgtggcaagtgagcctgaacgaacccagtcggacgaggagcttggagatccctccaagaacaaggc agccatctgtgagtggcttcccagtggtctctccagcagtcccagcaagccctgctacctcctgggagggag caccatccggaacaagaccatctactccagcatggggaaggcagcaccatgctggacccccttcaacaa gcagatacccaaggccatggggagtgcctcacccaccagtccatccagagactaaacggttcctgtatagtt caggaggcaaggaacgcctgcgaccctcttttctgctgagtgcactgcgaccttccctgtctggagcacgaa agctggtggagactatcttcctgggaagccgcccttggatgccaggaaccccacggagactgaggcgcct gcctcagcggtactggcgaatgagaccactgtttcaggaactgctgggaaaccacgccaggtgcccatatc gcgtgctgctgaaaacacattgtccactgcgggcaatggtgactcccgaggcctccgtcaatcagagacac aagggagtgggaatttgcccacagggaagcgtggtcgcacctccacaggaacagacagactccactcgc ctggtgcagctgctgcgacagcatagctcccctggcaggtgtacgcttttctgcgagcatgtctgcggtggct ggtgcctacaggactgtggggaagccgccacaaccagcgacggttcctgcggaacgtgaagaagttcatc tctctgggcaagcatgccaaactgagtctgcaggagctgacctggaagatgtccgtgcgcgattgcacatgg ctgagaaggtctccaggagtgggatgcgtgcctgctgcagaacaccgccgacgggaggaaattctggcca aattcctggtgtggctgatgagtcatatctacgtggtcaagctgctgcggtcattcttttatgtgaccgagactacc tttcagaagaaccgactgttctttttatcggaaatcagtgtggagccagctgcagtccatcggcattcgccagct gctgaacagcgtgcagctgcgagagctgagtgaggcagaagtcagaaggcaccgcgaagcacgacctg ccctgctgacttcaaggctgcgcttcatccctaaaccaagcggcctgaggccaattgtgaacatggactacat catggggggctcgcaccttccgccgagataagaaagtgcagagactgacctcaaggctgaagacactgttta gcgtgctgaattatgagagagctcggagacctagtctgctgggagcatcaatgctgggcctggacgatattc accgggcatggagaaccttcgtgctgcgaatccgggcacagaacccacctccacagctgtactttgtgaag gtcgccattactggcgcttatgacaccatcccccaggataggctggtggaggtcatcgcctccatcatcaagc ctcaggaatctacatactgcgtgaggcgctatgctgtggtccagaagactgcacgcgggcacgtgcgaaag gctttcaaatcccatgtctctaccctgacagacctgcagccatacatgagacagtttgtggagaggctgcagg aaacaagcccctgcgcgatgcagtggtcattgagcagtctagttcactgaacgaagctagctcctctctgttc cacctgtttctgcggctgatgcacaatcatgtggtcagaatcaggggcaaatcttacatccagtgtcaggggat tccccaaggaagtatcctgtcaaccctgctgtgcagcctgtgctatggggacatggagcgcaagctgttcccc gggatccgacgggatggactgctgctgcggctggtggacgatttcctgctggtcacccctcacctgacacag gcccagacttttctgagaaccctggtgaaaggcgtcccagagtacgggtgcgtggtcaacctgaggaagac
```

-continued

```
tgtggtcaatttccccgtggaagacggggctctgggatccaccgcaccactgcagctgcctgcacatggact gtttccttggtgtggactgctgctggacactagaaccctggaggtgagttcagattacagctcctatgcccgga cttcaattagagctagcctgaccttctccagaggctttaagccagggaggaacatgagaaggaaactgctg gccgtgctgaggctgaagtgccacgctctgtttctggacctgcaggtgaacagcatccagaccgtctacaca aatatctataaaattctgctgctgcaggcctacagattccatgcttgcgtgctgcagctgcccttcaaccagcag gtctggaagaatccctccttctttctgagagtgatcgctgataccgcatctctgtgctatagtatcctgaaggcca aaaatgctggactgtctctgggagcaaaaggagcagctggaccactgcctagtgaggcagtgcggtggct gtgcctgcaggccttcctgctgaagctgacaagacacagcgtgacttacgtcccactgctgggcgcactgag gactgcccagacccagctgtccaggcagctgcctcgcacaactctgacagccctggaagcagccgctaac ccagcactgaccgccgacttcaaaacaattctggat
```

The new conTRT amino acid consensus sequence (SEQ ID NO:1) (FIGS. 1-3) is:

```
MPRAPRCRAVRALLRSRYREVLPLATFLRRLGPQGWRLVRRGDPAA

FRALVAQCLVCVPWGARPPPAAPSFRQVSCLKELVARVLQRLCERGAKN

VLAFGFALLDGARGGPPVAFTTSVRSYLPNTVTDTLRGSGAWGLLLRRV

GDDVLVHLLARCALFLLVAPSCAYQVCGPPLYQLGAPTSLRPPPPASPP

RRRLPGLRAWNHAVRDLRVTRQLQNSGARRRRGSPSSSLPLPKRPRRSV

ASEPERTPVGRGAWRSPPRTRQPSVSGFPVVSPAVPASPATSWEGAPSG

TRPSTPAWGRQHHAGPPSTSRYPRPWGVPHPPVHPETKRFLYSSGGKER

LRPSFLLSALRPSLSGARKLVETIFLGSRPWMPGTPRRLRRLPQRYWRM

RPLFQELLGNHARCPYRVLLKTHCPLRAMVTPEASVNQRHKGVGICPQG

SVVAPPQEQTDSTRLVQLLRQHSSPWQVYAFLRACLRWLVPTGLWGSRH

NQRRFLRNVKKFISLGKHAKLSLQELTWKMSVRDCTWLRRSPGVGCVPA

AEHRRREEILAKFLVWLMSHIYVVKLLRSFFYVTETTFQKNRLFFYRKS

VWSQLQSIGIRQLLNSVQLRELSEAEVRRHREARPALLTSRLRFIPKPS

GLRPIVNMDYIMGARTFRRDKKVQRLTSRLKTLFSVLNYERARRPSLLG

ASMLGLDDIHRAWRTFVLRIRAQNPPPQLYFVKVAITGAYDTIPQDRLV

EVIASIIKPQESTYCVRRYAVVQKTARGHVRKAFKSHVSTLTDLQPYMR

QFVERLQETSPLRDAVVIEQSSSLNEASSSLFHLFLRLMHNHVVRIRGK

SYIQCQGIPQGSILSTLLCSLCYGDMERKLFPGIRRDGLLLRLVDDFLL

VTPHLTQAQTFLRTLVKGVPEYGCVVNLRKTVVNFPVEDGALGSTAPLQ

LPAHGLFPWCGLLLDTRTLEVSSDYSSYARTSIRASLTFSRGFKPGRNM

RRKLLAVLRLKCHALFLDLQVNSIQTVYTNIYKILLLQAYRFHACVLQL

PFNQQVWKNPSFFLRVIADTASLCYSILKAKNAGLSLGAKGAAGPLPSE

AVRWLCLQAFLLKLTRHSVTYVPLLGALRTAQTQLSRQLPRTTLTALEA

AANPALTADFKTILD
```

Evaluation of the Immunogenicity of the CaHu, HuCa and conTRT Sequences.

For the purpose of evaluating the cell-mediated immune response induced by the CaHu, HuCa and conTRT constructs, a genetic vaccination approach based on electroporation into the skeletal muscle (DNA-EP) of wild-type mice was adopted. This vaccination technique enables the use of laboratory-engineered constructs of different sizes and does not induce a neutralising response as in the case of viral vectors, thus making it possible to repeat the vaccinations a number of times. The immunisation protocol consisted in 4 injections, into the quadriceps of Balb/c mice, of 50 μg of the pTK1A-tPA-hTERT-LTB, pTK1A-tPA-dTERT-LTB, pTK1A-CaHu-PFTG, pTK1A-HuCa-PFTG and pTK1A-conTRT-PFTG constructs, spaced apart from one another by 1 week. In detail, the vector used is the pTK1A vector. The pTK1A expression vector comprises the promoter and intron A from human cytomegalovirus (CMV), a polylinker site for the cloning and bovine growth hormone (bGH) as a polyA for the transcription termination. Furthermore, the first two constructs pTK1A-tPA-hTERT-LTB and pTK1A-tPA-dTERT-LTB contain, in addition to the gene for human and dog telomerase, the leader sequence of tissue plasminogen activator (tPA), a signal sequence that favours the secretion of the protein of interest, and the sequence of lymphotoxin beta (LTB), which increases the immune response to the vector. The leader sequence of tissue plasminogen activator (TPA) is ATGGATGCAAT-GAAGAGAGGGCTCTGCTGTGTGCTGCTGCTGTGTG-GAG CAGTCTTCGTTTCGCCCAGC (SEQ ID NO:27), which encodes for the amino acid sequence MDAMKR-GLCCVLLLCGAVFVSPS (SEQ ID NO:28).

The other three constructs pTK1A-CaHu-PFTG, pTK1A-HuCa-PFTG and pTK1A-conTRT-PFTG comprise, in addition to the chimeric sequences CaHu and HuCA or the TRT consensus sequence, the PFTG sequence, which increases the immune response to the vector.

The DNA was formulated in phosphate-buffered saline (PBS) at a concentration of 1 mg/ml. DNA-EP was performed with a BTX 830 electroporator and flat electrodes with a distance of 0.5 cm (BTX, Harward apparatus), under the following electric conditions in the Low Voltage mode: 2 pulses of 60 msec at 100V, 250 msec pause between pulses. In order to measure the immune response induced by the vaccine, the number of splenocytes (expressed as spot-forming cells, SFC per million) secreting IFN was determined by means of the ELISpot technique, after 16 hours of stimulation with pools A, B, C and D of 15-mer peptides and overlapping by 11 amino acid residues both of the hTERT protein and of the dTERT protein. In particular, pool A comprises the amino acids 1-296; pool B comprises the amino acids 297-587; pool C comprises the amino acids 588-867; and pool D comprises the amino acids 868-1139. The splenocytes were isolated from wild-type mice vaccinated, by electroporation, with the hTERT, dTERT, CaHu, HuCa and conTRT vaccines.

As may be seen from FIG. 2, the mice immunised with pTK1-hTERT responded to the vaccine (mean response of the group greater than 50 SFC) when stimulated with the pools of hTERT peptides (above all pools A and D), whilst the response to the pools of dTERT peptides was very low or absent. In contrast, the mice immunised with pTK1-dTERT responded to the vaccine after stimulation with the dTERT pools (in particular pools A, C and D), but not with the hTERT pools. As regards the mice immunised with the pTK1-CaHu construct, a substantial response was observed only after stimulation with pool D of hTERT, whereas in the mice immunised with the pTK1-HuCa construct, no response towards any pool of peptides was detected. Finally, splenocytes isolated from mice immunised with the pTK1-conTRT-PFTG construct showed a substantial response after stimulation both with pool A of hTERT peptides and with pools A and D of dTERT peptides. These results indicate that the construct with the conTRT consensus sequence is strongly immunogenic and capable of arousing new specificities against the antigen telomerase, of both the human type and canine type.

Evaluation of the Antitumour Effect of the conTRT Sequence in Mice with Tumours.

For the purpose of evaluating the antitumour effect of the conTRT vaccine, Balb/c mice received three doses of the conTRT vaccine at two week intervals following a prophylactic vaccination protocol and were then injected with tumour cells of colon carcinoma (CT26) expressing human telomerase. As shown by FIG. 3, the vaccinated mice demonstrated less tumour growth compared to unvaccinated mice.

Evaluation of the Immunogenicity of the conTRT Sequence in Healthy Dogs and Dogs with Lymphoma.

Figure 4:
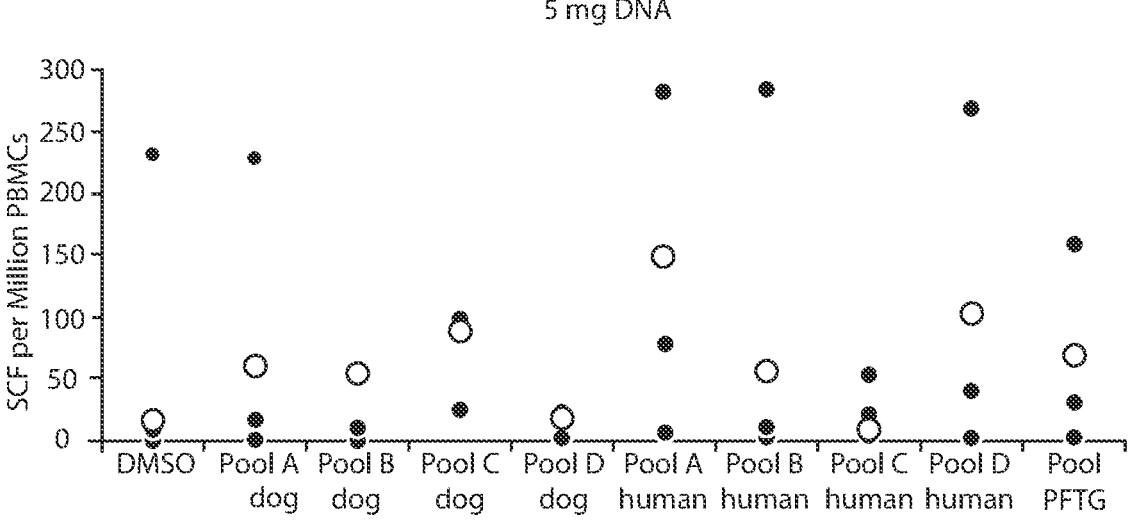
FIG. 4 shows the number of PBMCs isolated from healthy dogs and secreting IFNγ determined by means of the ELIS-pot technique, after 16 hours of stimulation with pools A, B, C and D of 15-mer peptides and overlapping by 11 amino acid residues both of the hTERT protein and of the dTERT protein. The graph shows the specific immune response for dog and human telomerase measured in the group of dogs vaccinated with 5 mg of DNA 4 weeks after the last vaccination.

For the purpose of determining the minimum immunogenic dose of the DNA produced, a clinical study was conducted on 9 healthy dogs of the beagle breed (6 males and 3 females reared and treated at Meditox cro-Czech Republic) vaccinated with a single intramuscular injection followed by electroporation with tapered doses of DNA, in particular 5 mg, 1 mg and 0.3 mg of plasmid DNA. The animals received three doses of vaccine every two weeks and peripheral blood samples were taken before every vaccination and at the end of the study (one month after the last dose of vaccine) in order to isolate the PBMCs (peripheral blood mononuclear cells). With the aim of identifying the minimal dose of DNA capable of inducing the maximum immune response specific for the consensus telomerase, the PBMCs were then analysed for the induction of an immune response by means of the ELISPOT assay, the immunological assay most widely used to evaluate vaccines in clinical studies in view of its high sensitivity. Briefly, the PBMCs were stimulated with different pools of immunogenic peptides, of both dog and human telomerase, and the production of IFN□ was then measured in order to evaluate the T-cell mediated immune response specific for telomerase. Prior to the start of the clinical study, at time zero, the possible presence of a response against telomerase was measured by ELISPOT and none was detected in any of the dogs treated. After two doses of DNA, in the group of dogs vaccinated with the maximum dose of 5 mg of DNA, the immune response specific for dog telomerase (measured after stimulation of the PBMCs with the pools of dog telomerase peptides, A, B, C and D) and for human telomerase (measured after stimulation of the PBMCs with the pools of human telomerase peptides, A, B, C and D) was still very low, if not absent. In the groups vaccinated with 1 and 0.3 mg doses, no telomerase-specific response was detected. In contrast, as shown in FIG. 4, 4 weeks after the third and last vaccination dose, in the group of dogs vaccinated with the maximum dose of DNA (5 mg), a substantial response was measured, both towards the pools of dog telomerase and towards the pools of human telomerase, thus confirming the choice of that vaccination scheme as optimal for obtaining, after a 4-week period, a greater specific response, and demonstrating, in particular, the effectiveness of the genetic vaccine pTK1A-conTRT-PFTG in inducing a telomerase-specific immune response. Furthermore, a considerable immune response specific for the PFTG protein was also measured in the same group. In the group of dogs vaccinated with an intermediate dose (1 mg), the measured response was considerably lower, whilst no response was detected in the group of dogs vaccinated with the minimum dose (0.3 mg), thus suggesting that 5 mg represents the optimal dose for inducing an efficient immune response.

The same vaccination protocol was used in three dogs affected by lymphoma expressing dog telomerase (FIG. 5). Four weeks after the last vaccination PBMCs were isolated from peripheral blood and the telomerase-specific immune response was measured by measuring the cells secreting IFN, after stimulation with the pools of dogTERT peptides. In particular, a substantial telomerase-specific response towards pool B of dogTERT was measured.

What is claimed is:

1. A nucleotide sequence encoding an amino acid consensus sequence of the antigen telomerase comprising sequence SEQ ID NO:1, wherein the nucleotide sequence comprises the nucleotide sequence SEQ ID NO: 4, or a sequence having a sequence identity of at least 80% with respect to SEQ ID NO:4, and a nucleotide sequence encoding the profilin-like protein of *Toxoplasma Gondii*, wherein the nucleotide sequence encoding the profilin-like protein of *Toxoplasma Gondii* comprises SEQ ID NO: 31.

2. An expression vector comprising the nucleotide sequence as defined in claim 1.

3. The expression vector according to claim 2, wherein said vector is selected from the group consisting of a plasmid, an RNA, a replicating RNA, amplicons obtained by PCR, and a viral vector.

4. A DNA, or RNA based vaccine comprising the nucleotide sequence of claim 1.

5. A method of vaccinating a subject against telomerase-expressing tumors or treating a subject having a telomerase-expressing tumors, comprising administering the vaccine of claim 4 to the subject.

6. The method according to claim 5, wherein the vaccine is administered to the subject by electroporation.

7. A pharmaceutical composition comprising a nucleotide sequence as defined in claim 1, in combination with one or more excipients and/or adjuvants.

8. The nucleotide sequence according to claim 1, wherein the amino acid sequence further comprises one or more leader sequences.

9. The nucleotide sequence according to claim 8, wherein the one or more leader sequence is a secretion leader sequence of a protein selected from the group consisting of tissue plasminogen activator (TPA), IgK, growth hormone, serum albumin, and alkaline phosphatase.

10. The nucleotide sequence according to claim 1, wherein the amino acid sequence further comprises one or more immunomodulating amino acid sequences.

11. The nucleotide sequence according to claim 10, wherein the one or more immunomodulating amino acid sequences are selected from the group consisting of the fragment crystallisable (Fc) region, profilin-like protein of *Toxoplasma Gondii* (PFTG) or a functional fragment derived therefrom, the B subunit of the heat-labile toxin of *Escherichia Coli* (LTB) and the tetanus toxin (TT).

* * * * *

SEQUENCE LISTING

```
<160> NUMBER OF SEQ ID NOS: 31

<210> SEQ ID NO 1
<211> LENGTH: 1139
<212> TYPE: PRT
<213> ORGANISM: Artificial
<220> FEATURE:
<223> OTHER INFORMATION: consensus sequence of telomerase antigen

<400> SEQUENCE: 1

Met Pro Arg Ala Pro Arg Cys Arg Ala Val Arg Ala Leu Leu Arg Ser
1               5                   10                  15

Arg Tyr Arg Glu Val Leu Pro Leu Ala Thr Phe Leu Arg Arg Leu Gly
            20                  25                  30

Pro Gln Gly Trp Arg Leu Val Arg Arg Gly Asp Pro Ala Ala Phe Arg
        35                  40                  45
```

-continued

```
Ala Leu Val Ala Gln Cys Leu Val Cys Val Pro Trp Gly Ala Arg Pro
    50              55              60

Pro Pro Ala Ala Pro Ser Phe Arg Gln Val Ser Cys Leu Lys Glu Leu
65              70              75              80

Val Ala Arg Val Leu Gln Arg Leu Cys Glu Arg Gly Ala Lys Asn Val
            85              90              95

Leu Ala Phe Gly Phe Ala Leu Leu Asp Gly Ala Arg Gly Gly Pro Pro
            100             105             110

Val Ala Phe Thr Thr Ser Val Arg Ser Tyr Leu Pro Asn Thr Val Thr
            115             120             125

Asp Thr Leu Arg Gly Ser Gly Ala Trp Gly Leu Leu Leu Arg Arg Val
    130             135             140

Gly Asp Asp Val Leu Val His Leu Leu Ala Arg Cys Ala Leu Phe Leu
145             150             155             160

Leu Val Ala Pro Ser Cys Ala Tyr Gln Val Cys Gly Pro Pro Leu Tyr
            165             170             175

Gln Leu Gly Ala Pro Thr Ser Leu Arg Pro Pro Pro Ala Ser Pro
            180             185             190

Pro Arg Arg Arg Leu Pro Gly Leu Arg Ala Trp Asn His Ala Val Arg
            195             200             205

Asp Leu Arg Val Thr Arg Gln Leu Gln Asn Ser Gly Ala Arg Arg Arg
    210             215             220

Arg Gly Ser Pro Ser Ser Ser Leu Pro Leu Pro Lys Arg Pro Arg Arg
225             230             235             240

Ser Val Ala Ser Glu Pro Glu Arg Thr Pro Val Gly Arg Gly Ala Trp
            245             250             255

Arg Ser Pro Pro Arg Thr Arg Gln Pro Ser Val Ser Gly Phe Pro Val
            260             265             270

Val Ser Pro Ala Val Pro Ala Ser Pro Ala Thr Ser Trp Glu Gly Ala
            275             280             285

Pro Ser Gly Thr Arg Pro Ser Thr Pro Ala Trp Gly Arg Gln His His
    290             295             300

Ala Gly Pro Pro Ser Thr Ser Arg Tyr Pro Arg Pro Trp Gly Val Pro
305             310             315             320

His Pro Pro Val His Pro Glu Thr Lys Arg Phe Leu Tyr Ser Ser Gly
            325             330             335

Gly Lys Glu Arg Leu Arg Pro Ser Phe Leu Leu Ser Ala Leu Arg Pro
            340             345             350

Ser Leu Ser Gly Ala Arg Lys Leu Val Glu Thr Ile Phe Leu Gly Ser
            355             360             365

Arg Pro Trp Met Pro Gly Thr Pro Arg Arg Leu Arg Arg Leu Pro Gln
    370             375             380

Arg Tyr Trp Arg Met Arg Pro Leu Phe Gln Glu Leu Leu Gly Asn His
385             390             395             400

Ala Arg Cys Pro Tyr Arg Val Leu Leu Lys Thr His Cys Pro Leu Arg
            405             410             415

Ala Met Val Thr Pro Glu Ala Ser Val Asn Gln Arg His Lys Gly Val
            420             425             430

Gly Ile Cys Pro Gln Gly Ser Val Val Ala Pro Pro Gln Glu Gln Thr
            435             440             445

Asp Ser Thr Arg Leu Val Gln Leu Leu Arg Gln His Ser Ser Pro Trp
    450             455             460

Gln Val Tyr Ala Phe Leu Arg Ala Cys Leu Arg Trp Leu Val Pro Thr
```

-continued

```
465               470               475               480

Gly Leu Trp Gly Ser Arg His Asn Gln Arg Arg Phe Leu Arg Asn Val
                 485               490               495

Lys Lys Phe Ile Ser Leu Gly Lys His Ala Lys Leu Ser Leu Gln Glu
                 500               505               510

Leu Thr Trp Lys Met Ser Val Arg Asp Cys Thr Trp Leu Arg Arg Ser
                 515               520               525

Pro Gly Val Gly Cys Val Pro Ala Ala Glu His Arg Arg Arg Glu Glu
        530               535               540

Ile Leu Ala Lys Phe Leu Val Trp Leu Met Ser His Ile Tyr Val Val
545               550               555               560

Lys Leu Leu Arg Ser Phe Phe Tyr Val Thr Glu Thr Thr Phe Gln Lys
                 565               570               575

Asn Arg Leu Phe Phe Tyr Arg Lys Ser Val Trp Ser Gln Leu Gln Ser
                 580               585               590

Ile Gly Ile Arg Gln Leu Leu Asn Ser Val Gln Leu Arg Glu Leu Ser
             595               600               605

Glu Ala Glu Val Arg Arg His Arg Glu Ala Arg Pro Ala Leu Leu Thr
        610               615               620

Ser Arg Leu Arg Phe Ile Pro Lys Pro Ser Gly Leu Arg Pro Ile Val
625               630               635               640

Asn Met Asp Tyr Ile Met Gly Ala Arg Thr Phe Arg Arg Asp Lys Lys
                 645               650               655

Val Gln Arg Leu Thr Ser Arg Leu Lys Thr Leu Phe Ser Val Leu Asn
                 660               665               670

Tyr Glu Arg Ala Arg Arg Pro Ser Leu Leu Gly Ala Ser Met Leu Gly
             675               680               685

Leu Asp Asp Ile His Arg Ala Trp Arg Thr Phe Val Leu Arg Ile Arg
        690               695               700

Ala Gln Asn Pro Pro Gln Leu Tyr Phe Val Lys Val Ala Ile Thr
705               710               715               720

Gly Ala Tyr Asp Thr Ile Pro Gln Asp Arg Leu Val Glu Val Ile Ala
                 725               730               735

Ser Ile Ile Lys Pro Gln Glu Ser Thr Tyr Cys Val Arg Arg Tyr Ala
                 740               745               750

Val Val Gln Lys Thr Ala Arg Gly His Val Arg Lys Ala Phe Lys Ser
             755               760               765

His Val Ser Thr Leu Thr Asp Leu Gln Pro Tyr Met Arg Gln Phe Val
        770               775               780

Glu Arg Leu Gln Glu Thr Ser Pro Leu Arg Asp Ala Val Val Ile Glu
785               790               795               800

Gln Ser Ser Ser Leu Asn Glu Ala Ser Ser Ser Leu Phe His Leu Phe
                 805               810               815

Leu Arg Leu Met His Asn His Val Val Arg Ile Arg Gly Lys Ser Tyr
                 820               825               830

Ile Gln Cys Gln Gly Ile Pro Gln Gly Ser Ile Leu Ser Thr Leu Leu
             835               840               845

Cys Ser Leu Cys Tyr Gly Asp Met Glu Arg Lys Leu Phe Pro Gly Ile
        850               855               860

Arg Arg Asp Gly Leu Leu Leu Arg Leu Val Asp Asp Phe Leu Leu Val
865               870               875               880

Thr Pro His Leu Thr Gln Ala Gln Thr Phe Leu Arg Thr Leu Val Lys
                 885               890               895
```

```
Gly Val Pro Glu Tyr Gly Cys Val Val Asn Leu Arg Lys Thr Val Val
            900             905             910

Asn Phe Pro Val Glu Asp Gly Ala Leu Gly Ser Thr Ala Pro Leu Gln
            915             920             925

Leu Pro Ala His Gly Leu Phe Pro Trp Cys Gly Leu Leu Leu Asp Thr
            930             935             940

Arg Thr Leu Glu Val Ser Ser Asp Tyr Ser Ser Tyr Ala Arg Thr Ser
945             950             955             960

Ile Arg Ala Ser Leu Thr Phe Ser Arg Gly Phe Lys Pro Gly Arg Asn
                965             970             975

Met Arg Arg Lys Leu Leu Ala Val Leu Arg Leu Lys Cys His Ala Leu
            980             985             990

Phe Leu Asp Leu Gln Val Asn Ser  Ile Gln Thr Val Tyr  Thr Asn Ile
            995             1000            1005

Tyr Lys  Ile Leu Leu Leu Gln  Ala Tyr Arg Phe His  Ala Cys Val
    1010            1015            1020

Leu Gln  Leu Pro Phe Asn Gln  Gln Val Trp Lys Asn  Pro Ser Phe
    1025            1030            1035

Phe Leu  Arg Val Ile Ala Asp  Thr Ala Ser Leu Cys  Tyr Ser Ile
    1040            1045            1050

Leu Lys  Ala Lys Asn Ala Gly  Leu Ser Leu Gly Ala  Lys Gly Ala
    1055            1060            1065

Ala Gly  Pro Leu Pro Ser Glu  Ala Val Arg Trp Leu  Cys Leu Gln
    1070            1075            1080

Ala Phe  Leu Leu Lys Leu Thr  Arg His Ser Val Thr  Tyr Val Pro
    1085            1090            1095

Leu Leu  Gly Ala Leu Arg Thr  Ala Gln Thr Gln Leu  Ser Arg Gln
    1100            1105            1110

Leu Pro  Arg Thr Thr Leu Thr  Ala Leu Glu Ala Ala  Ala Asn Pro
    1115            1120            1125

Ala Leu  Thr Ala Asp Phe Lys  Thr Ile Leu Asp
    1130            1135
```

<210> SEQ ID NO 2
<211> LENGTH: 1122
<212> TYPE: PRT
<213> ORGANISM: Artificial
<220> FEATURE:
<223> OTHER INFORMATION: chimeric fusion protein of dog and human
    telomerase

<400> SEQUENCE: 2

```
Met Pro Arg Ala Pro Arg Cys Arg Ala Val Arg Ala Leu Leu Arg Gly
1               5               10              15

Arg Tyr Arg Glu Val Leu Pro Leu Ala Thr Phe Leu Arg Arg Leu Gly
            20              25              30

Pro Pro Gly Arg Leu Leu Val Arg Arg Gly Asp Pro Ala Ala Phe Arg
            35              40              45

Ala Leu Val Ala Gln Cys Leu Val Cys Val Pro Trp Gly Ala Arg Pro
    50              55              60

Pro Pro Ala Ala Pro Cys Phe Arg Gln Val Ser Cys Leu Lys Glu Leu
65              70              75              80

Val Ala Arg Val Val Gln Arg Leu Cys Glu Arg Gly Ala Arg Asn Val
                85              90              95

Leu Ala Phe Gly Phe Ala Leu Leu Asp Gly Ala Arg Gly Gly Pro Pro
```

-continued

```
               100              105              110
Val Ala Phe Thr Thr Ser Val Arg Ser Tyr Leu Pro Asn Thr Val Thr
           115              120              125

Glu Thr Leu Arg Gly Ser Gly Ala Trp Gly Leu Leu Leu Arg Arg Val
       130              135              140

Gly Asp Asp Val Leu Thr His Leu Leu Ala Arg Cys Ala Leu Tyr Leu
145              150              155              160

Leu Val Ala Pro Ser Cys Ala Tyr Gln Val Cys Gly Pro Pro Leu Tyr
               165              170              175

Asp Leu Cys Ala Pro Ala Ser Leu Pro Leu Pro Ala Pro Gly Leu Pro
           180              185              190

Gly Leu Pro Gly Leu Pro Gly Leu Gly Ala Gly Ala Gly Ala Ser Ala
           195              200              205

Asp Leu Arg Pro Thr Arg Gln Ala Gln Asn Ser Gly Ala Arg Arg Arg
       210              215              220

Arg Gly Ser Pro Gly Ser Gly Val Pro Leu Ala Lys Arg Pro Arg Arg
225              230              235              240

Ser Val Ala Ser Glu Pro Glu Arg Gly Ala His Arg Ser Phe Pro Arg
               245              250              255

Ala Gln Gln Pro Pro Val Ser Glu Ala Pro Ala Val Thr Pro Ala Val
           260              265              270

Ala Ala Ser Pro Ala Ala Ser Trp Glu Gly Gly Pro Pro Gly Thr Arg
           275              280              285

Pro Thr Thr Pro Ala Trp His Pro Tyr Pro Gly Pro Gln Gly Val Pro
       290              295              300

His Asp Pro Ala His Pro Glu Thr Lys Arg Phe Leu Tyr Cys Ser Gly
305              310              315              320

Gly Arg Glu Arg Leu Arg Pro Ser Phe Leu Leu Ser Ala Leu Pro Pro
           325              330              335

Thr Leu Ser Gly Ala Arg Lys Leu Val Glu Thr Ile Phe Leu Gly Ser
           340              345              350

Ala Pro Gln Lys Pro Gly Ala Ala Arg Arg Met Arg Arg Leu Pro Ala
           355              360              365

Arg Tyr Trp Arg Met Arg Pro Leu Phe Gln Glu Leu Leu Gly Asn His
       370              375              380

Ala Arg Cys Pro Tyr Arg Ala Leu Leu Arg Thr His Cys Pro Leu Arg
385              390              395              400

Ala Met Ala Ala Lys Glu Gly Ser Gly Asn Gln Ala His Arg Gly Val
           405              410              415

Gly Ile Cys Pro Leu Glu Arg Pro Val Ala Ala Pro Gln Glu Gln Thr
           420              425              430

Asp Ser Thr Arg Leu Val Gln Leu Leu Arg Gln His Ser Ser Pro Trp
           435              440              445

Gln Val Tyr Ala Phe Leu Arg Ala Cys Leu Cys Trp Leu Val Pro Thr
       450              455              460

Gly Leu Trp Gly Ser Arg His Asn Gln Arg Arg Phe Leu Arg Asn Val
465              470              475              480

Lys Lys Phe Ile Ser Leu Gly Lys His Ala Lys Leu Ser Leu Gln Glu
               485              490              495

Leu Thr Trp Lys Met Lys Val Arg Asp Cys Thr Trp Leu His Gly Asn
           500              505              510

Pro Gly Ala Cys Cys Val Pro Ala Ala Glu His Arg Arg Arg Glu Glu
           515              520              525
```

-continued

```
Ile Leu Ala Arg Phe Leu Val Leu Val Asp Gly His Ile Tyr Val Val
    530                 535                 540

Lys Leu Leu Arg Ser Phe Phe Tyr Val Thr Glu Thr Thr Phe Gln Lys
545                 550                 555                 560

Asn Arg Leu Phe Phe Tyr Arg Lys Ser Val Trp Ser Gln Leu Gln Ser
                565                 570                 575

Ile Gly Ile Arg Gln Leu Phe Asn Ser Val His Leu Arg Glu Leu Ser
            580                 585                 590

Glu Ala Glu Val Arg Arg His Arg Glu Ala Arg Pro Ala Leu Leu Thr
        595                 600                 605

Ser Arg Leu Arg Phe Leu Pro Lys Pro Ser Gly Leu Arg Pro Ile Val
    610                 615                 620

Asn Met Asp Tyr Ile Met Gly Ala Arg Thr Phe His Arg Asp Lys Lys
625                 630                 635                 640

Val Gln His Leu Thr Ser Gln Leu Lys Thr Leu Phe Ser Val Leu Asn
                645                 650                 655

Tyr Glu Arg Ala Arg Arg Pro Ser Leu Leu Gly Ala Ser Met Leu Gly
            660                 665                 670

Met Asp Asp Ile His Arg Ala Trp Arg Thr Phe Val Leu Arg Ile Arg
            675                 680                 685

Ala Gln Asn Pro Ala Pro Gln Leu Tyr Phe Val Lys Val Ala Ile Thr
    690                 695                 700

Gly Ala Tyr Asp Thr Ile Pro Gln Asp Arg Leu Thr Glu Val Ile Ala
705                 710                 715                 720

Ser Ile Ile Lys Pro Gln Asn Thr Tyr Cys Val Arg Arg Tyr Ala Val
                725                 730                 735

Val Gln Lys Ala Ala His Gly His Val Arg Lys Ala Phe Lys Ser His
            740                 745                 750

Val Ser Thr Leu Thr Asp Leu Gln Pro Tyr Met Arg Gln Phe Val Ala
            755                 760                 765

His Leu Gln Glu Thr Ser Pro Leu Arg Asp Ala Val Val Ile Glu Gln
    770                 775                 780

Ser Ser Ser Leu Asn Glu Ala Ser Ser Gly Leu Phe Asp Val Phe Leu
785                 790                 795                 800

Arg Phe Met Cys His His Ala Val Arg Ile Arg Gly Lys Ser Tyr Val
                805                 810                 815

Gln Cys Gln Gly Ile Pro Gln Gly Ser Ile Leu Ser Thr Leu Leu Cys
            820                 825                 830

Ser Leu Cys Tyr Gly Asp Met Glu Asn Lys Leu Phe Ala Gly Ile Arg
            835                 840                 845

Arg Asp Gly Leu Leu Leu Arg Leu Val Asp Asp Phe Leu Leu Val Thr
    850                 855                 860

Pro His Leu Thr His Ala Lys Thr Phe Leu Arg Thr Leu Val Arg Gly
865                 870                 875                 880

Val Pro Glu Tyr Gly Cys Val Val Asn Leu Arg Lys Thr Val Val Asn
                885                 890                 895

Phe Pro Val Glu Asp Glu Ala Leu Gly Gly Thr Ala Phe Val Gln Met
            900                 905                 910

Pro Ala His Gly Leu Phe Pro Trp Cys Gly Leu Leu Leu Asp Thr Arg
            915                 920                 925

Thr Leu Glu Val Gln Ser Asp Tyr Ser Ser Tyr Ala Arg Thr Ser Ile
    930                 935                 940
```

```
Arg Ala Ser Leu Thr Phe Asn Arg Gly Phe Lys Ala Gly Arg Asn Met
945             950             955             960

Arg Arg Lys Leu Phe Gly Val Leu Arg Leu Lys Cys His Ser Leu Phe
            965             970             975

Leu Asp Leu Gln Val Asn Ser Leu Gln Thr Val Cys Thr Asn Ile Tyr
            980             985             990

Lys Ile Leu Leu Leu Gln Ala Tyr  Arg Phe His Ala Cys  Val Leu Gln
        995             1000            1005

Leu Pro  Phe His Gln Gln Val  Trp Lys Asn Pro Thr  Phe Phe Leu
    1010            1015            1020

Arg Val  Ile Ser Asp Thr Ala  Ser Leu Cys Tyr Ser  Ile Leu Lys
    1025            1030            1035

Ala Lys  Asn Ala Gly Met Ser  Leu Gly Ala Lys Gly  Ala Ala Gly
    1040            1045            1050

Pro Leu  Pro Ser Glu Ala Val  Gln Trp Leu Cys His  Gln Ala Phe
    1055            1060            1065

Leu Leu  Lys Leu Thr Arg His  Arg Val Thr Tyr Val  Pro Leu Leu
    1070            1075            1080

Gly Ser  Leu Arg Thr Ala Gln  Thr Gln Leu Ser Arg  Lys Leu Pro
    1085            1090            1095

Gly Thr  Thr Leu Thr Ala Leu  Glu Ala Ala Ala Asn  Pro Ala Leu
    1100            1105            1110

Pro Ser  Asp Phe Lys Thr Ile  Leu Asp
    1115            1120

<210> SEQ ID NO 3
<211> LENGTH: 1132
<212> TYPE: PRT
<213> ORGANISM: Artificial
<220> FEATURE:
<223> OTHER INFORMATION: chimeric fusion protein of human and dog
      telomerase

<400> SEQUENCE: 3

Pro Arg Ala Pro Arg Cys Arg Ala Val Arg Ser Leu Leu Arg Ser His
1               5               10              15

Tyr Arg Glu Val Leu Pro Leu Ala Thr Phe Val Arg Arg Leu Gly Pro
            20              25              30

Gln Gly Trp Arg Leu Val Gln Arg Gly Asp Pro Ala Ala Phe Arg Ala
        35              40              45

Leu Val Ala Gln Cys Leu Val Cys Val Pro Trp Asp Ala Arg Pro Pro
    50              55              60

Pro Ala Ala Pro Ser Phe Arg Gln Val Ser Cys Leu Lys Glu Leu Val
65              70              75              80

Ala Arg Val Leu Gln Arg Leu Cys Glu Arg Gly Ala Lys Asn Val Leu
            85              90              95

Ala Phe Gly Phe Ala Leu Leu Asp Gly Ala Arg Gly Gly Pro Pro Glu
            100             105             110

Ala Phe Thr Thr Ser Val Arg Ser Tyr Leu Pro Asn Thr Val Thr Asp
        115             120             125

Ala Leu Arg Gly Ser Gly Ala Trp Gly Leu Leu Leu Arg Arg Val Gly
        130             135             140

Asp Asp Val Leu Val His Leu Leu Ala Arg Cys Ala Leu Phe Val Leu
145             150             155             160

Val Ala Pro Ser Cys Ala Tyr Gln Val Cys Gly Pro Pro Leu Tyr Gln
            165             170             175
```

-continued

```
Leu Gly Ala Ala Thr Gln Ala Arg Pro Pro Pro His Ala Ser Gly Pro
            180                 185                 190

Arg Arg Arg Leu Gly Cys Glu Arg Ala Trp Asn His Ser Val Arg Glu
            195                 200                 205

Ala Gly Val Pro Leu Gly Leu Pro Ala Pro Gly Ala Arg Arg Arg Gly
            210                 215                 220

Gly Ser Ala Ser Arg Ser Leu Pro Leu Pro Lys Arg Pro Arg Arg Gly
225                 230                 235                 240

Ala Ala Pro Glu Pro Glu Arg Thr Pro Val Gly Gln Gly Ser Trp Ala
                245                 250                 255

His Pro Gly Arg Thr Arg Gly Pro Ser Asp Arg Gly Phe Cys Val Val
            260                 265                 270

Ser Pro Ala Arg Pro Ala Glu Glu Ala Thr Ser Leu Glu Gly Ala Leu
            275                 280                 285

Ser Gly Thr Arg His Ser His Pro Ser Val Gly Arg Gln His His Ala
            290                 295                 300

Gly Pro Pro Ser Thr Ser Arg Pro Pro Arg Pro Trp Asp Thr Pro Cys
305                 310                 315                 320

Pro Pro Val Tyr Ala Glu Thr Lys His Phe Leu Tyr Ser Ser Gly Asp
                325                 330                 335

Lys Glu Gln Leu Arg Pro Ser Phe Leu Leu Ser Ser Leu Arg Pro Ser
            340                 345                 350

Leu Thr Gly Ala Arg Arg Leu Val Glu Thr Ile Phe Leu Gly Ser Arg
            355                 360                 365

Pro Trp Met Pro Gly Thr Pro Arg Arg Leu Pro Arg Leu Pro Gln Arg
370                 375                 380

Tyr Trp Gln Met Arg Pro Leu Phe Leu Glu Leu Leu Gly Asn His Ala
385                 390                 395                 400

Gln Cys Pro Tyr Gly Val Leu Leu Lys Thr His Cys Pro Leu Arg Ala
                405                 410                 415

Ala Val Thr Pro Ala Ala Gly Val Cys Ala Arg Glu Lys Pro Gln Gly
            420                 425                 430

Ser Val Ala Ala Pro Glu Glu Glu Asp Thr Asp Pro Arg Arg Leu Val
            435                 440                 445

Gln Leu Leu Arg Gln His Ser Ser Pro Trp Gln Val Tyr Gly Phe Val
            450                 455                 460

Arg Ala Cys Leu Arg Arg Leu Val Pro Pro Gly Leu Trp Gly Ser Arg
465                 470                 475                 480

His Asn Glu Arg Arg Phe Leu Arg Asn Thr Lys Lys Phe Ile Ser Leu
                485                 490                 495

Gly Lys His Ala Lys Leu Ser Leu Gln Glu Leu Thr Trp Lys Met Ser
            500                 505                 510

Val Arg Asp Cys Ala Trp Leu Arg Arg Ser Pro Gly Val Gly Cys Val
            515                 520                 525

Pro Ala Ala Glu His Arg Leu Arg Glu Glu Ile Leu Ala Lys Phe Leu
            530                 535                 540

His Trp Leu Met Ser Val Tyr Val Val Glu Leu Leu Arg Ser Phe Phe
545                 550                 555                 560

Tyr Val Thr Glu Thr Thr Phe Gln Lys Asn Arg Leu Phe Phe Tyr Arg
                565                 570                 575

Lys Ser Val Trp Ser Lys Leu Gln Ser Ile Gly Ile Arg Gln His Leu
            580                 585                 590
```

-continued

```
Lys Arg Val Gln Leu Arg Glu Leu Ser Glu Ala Glu Val Arg Gln His
        595                 600             605

Arg Glu Ala Arg Pro Ala Leu Leu Thr Ser Arg Leu Arg Phe Ile Pro
        610                 615             620

Lys Pro Asp Gly Leu Arg Pro Ile Val Asn Met Asp Tyr Val Val Gly
625                 630                 635                 640

Ala Arg Thr Phe Arg Arg Glu Lys Arg Ala Glu Arg Leu Thr Ser Arg
                645                 650                 655

Val Lys Ala Leu Phe Ser Val Leu Asn Tyr Glu Arg Ala Arg Arg Pro
                660                 665                 670

Gly Leu Leu Gly Ala Ser Val Leu Gly Leu Asp Asp Ile His Arg Ala
                675                 680                 685

Trp Arg Thr Phe Val Leu Arg Val Arg Ala Gln Asp Pro Pro Pro Glu
        690                 695                 700

Leu Tyr Phe Val Lys Val Ala Ile Thr Gly Ala Tyr Asp Ala Leu Pro
705                 710                 715                 720

Gln Asp Arg Leu Val Glu Val Ile Ala Asn Val Ile Arg Pro Gln Glu
                725                 730                 735

Ser Thr Tyr Cys Val Arg His Tyr Ala Val Val Gln Arg Thr Ala Arg
                740                 745                 750

Gly His Val Arg Lys Ala Phe Lys Arg His Val Ser Thr Phe Ala Asp
                755                 760                 765

Leu Gln Pro Tyr Met Arg Gln Phe Val Glu Arg Leu Gln Glu Thr Ser
        770                 775                 780

Leu Leu Arg Asp Ala Val Val Ile Glu Gln Ser Ser Ser Leu Asn Glu
785                 790                 795                 800

Ala Gly Ser Ser Leu Phe His Leu Phe Leu Arg Leu Val His Asn His
                805                 810                 815

Val Val Arg Ile Gly Gly Lys Ser Tyr Ile Gln Cys Gln Gly Val Pro
                820                 825                 830

Gln Gly Ser Ile Leu Ser Thr Leu Leu Cys Ser Leu Cys Tyr Gly Asp
                835                 840                 845

Met Glu Arg Arg Leu Phe Pro Gly Ile Glu Gln Asp Gly Val Leu Leu
        850                 855                 860

Arg Leu Val Asp Asp Phe Leu Leu Val Thr Pro His Leu Thr Gln Ala
865                 870                 875                 880

Gln Ala Phe Leu Arg Thr Leu Val Lys Gly Val Pro Glu Tyr Gly Cys
                885                 890                 895

Arg Ala Asn Leu Gln Lys Thr Ala Val Asn Phe Pro Val Glu Asp Gly
                900                 905                 910

Ala Leu Gly Ser Ala Ala Pro Leu Gln Leu Pro Ala His Cys Leu Phe
                915                 920                 925

Pro Trp Cys Gly Leu Leu Leu Asp Thr Arg Thr Leu Glu Val Ser Cys
        930                 935                 940

Asp Tyr Ser Ser Tyr Ala His Thr Ser Ile Arg Ala Ser Leu Thr Phe
945                 950                 955                 960

Ser Gln Gly Ala Lys Pro Gly Arg Asn Met Arg Arg Lys Leu Leu Ala
                965                 970                 975

Val Leu Arg Leu Lys Cys Cys Ala Leu Phe Leu Asp Leu Gln Val Asn
                980                 985                 990

Gly Ile His Thr Val Tyr Met Asn  Val Tyr Lys Ile Phe  Leu Leu Gln
        995                 1000                1005

Ala Tyr  Arg Phe His Ala Cys  Val Leu Gln Leu Pro  Phe Asn Gln
```

-continued

```
         1010              1015              1020

Pro Val  Arg Lys Asn Pro Ser  Phe Phe Leu Arg Val  Ile Ala Asp
    1025             1030             1035

Thr Ala  Ser Cys Cys Tyr Ser  Leu Leu Lys Ala Arg  Asn Ala Gly
    1040             1045             1050

Leu Ser  Leu Gly Ala Lys Gly  Ala Ser Gly Leu Phe  Pro Ser Glu
    1055             1060             1065

Ala Ala  Arg Trp Leu Cys Leu  His Ala Phe Leu Leu  Lys Leu Ala
    1070             1075             1080

His His  Ser Gly Thr Tyr Arg  Cys Leu Leu Gly Ala  Leu Gln Ala
    1085             1090             1095

Ala Lys  Ala His Leu Ser Arg  Gln Leu Pro Arg Gly  Thr Leu Ala
    1100             1105             1110

Ala Leu  Glu Ala Ala Ala Asp  Pro Ser Leu Thr Ala  Asp Phe Lys
    1115             1120             1125

Thr Ile  Leu Asp
    1130

<210> SEQ ID NO 4
<211> LENGTH: 3471
<212> TYPE: DNA
<213> ORGANISM: Artificial
<220> FEATURE:
<223> OTHER INFORMATION: nucleotide sequence encoding SEQ ID NO:1

<400> SEQUENCE: 4
atgggatggt catgtattat tctgttcctg gtcgctaccg caaccggagt gcatagtcca     60 agagcccta gatgtcgagc cgtgagggca ctgctgcgca gccgataccg ggaggtgctg    120
cctctggcta ccttcctgcg gagactggga ccacagggat ggagactggt gaggcgaggg    180
gacccagcag cttttagggc tctggtcgca cagtgcctgg tgtgcgtgcc atggggagca    240
agaccacctc cagcagcccc ttcattcagg caggtgagct gcctgaaaga gctggtggct    300
agggtcctgc agcggctgtg cgaacgagga gcaaagaacg tgctggcttt cgggtttgca    360
ctgctggacg gagctagagg aggaccacct gtggccttca ccaccagcgt gcggagctat    420
ctgcccaata ccgtgacaga tactctgcga ggatccggag catggggact gctgctgcga    480
cgggtggggg acgatgtgct ggtccacctg ctggcacgat gcgctctgtt cctgctggtg    540
gccccttctt gcgcttacca ggtctgtgga ccacccctgt atcagctggg cgccccaaca    600
agtctgagac ctccaccccc tgcttcacca ccaagaaggc gcctgccagg actgagggca    660
tggaaccatg ccgtgcgcga cctgcgagtc actcgacagc tgcagaatag cggagcacga    720
cggagaaggg gatccccaag ctcctctctg ccactgccta agcgaccacg ccgatctgtg    780
gcaagtgagc ctgaacgaac cccagtcgga cgaggagctt ggagatcccc tccaagaaca    840
aggcagccat ctgtgagtgg cttcccagtg gtctctccag cagtcccagc aagccctgct    900
acctcctggg agggagcacc atccggaaca agaccatcta ctccagcatg gggaaggcag    960
caccatgctg gacccccttc aacaagcaga tacccaaggc catggggagt gcctcaccca   1020
ccagtccatc cagagactaa acggttcctg tatagttcag gaggcaagga acgcctgcga   1080
ccctcttttc tgctgagtgc actgcgacct tccctgtctg agcacgaaa gctggtggag   1140 actatcttcc tgggaagccg ccccttggatg ccaggaaccc cacggagact gaggcgcctg   1200
cctcagcggt actggcgaat gagaccactg tttcaggaac tgctgggaaa ccacgccag   1260 tgcccatatc gcgtgctgct gaaaacacat tgtccactgc gggcaatggt gactcccgag   1320
```

-continued

```
gcctccgtca atcagagaca caagggagtg ggaatttgcc cacagggaag cgtggtcgca      1380
cctccacagg aacagacaga ctccactcgc ctggtgcagc tgctgcgaca gcatagctcc      1440
ccctggcagg tgtacgcttt tctgcgagca tgtctgcggt ggctggtgcc tacaggactg      1500
tggggaagcc gccacaacca cgacggttc ctgcggaacg tgaagaagtt catctctctg       1560
ggcaagcatg ccaaactgag tctgcaggag ctgacctgga agatgtccgt gcgcgattgc      1620
acatggctga gaaggtctcc aggagtggga tgcgtgcctg ctgcagaaca ccgccgacgg      1680
gaggaaattc tggccaaatt cctggtgtgg ctgatgagtc atatctacgt ggtcaagctg      1740
ctgcggtcat tcttttatgt gaccgagact acctttcaga agaaccgact gttcttttat      1800
cggaaatcag tgtggagcca gctgcagtcc atcggcattc gccagctgct gaacagcgtg      1860
cagctgcgag agctgagtga ggcagaagtc agaaggcacc gcgaagcacg acctgccctg      1920
ctgacttcaa ggctgcgctt catccctaaa ccaagcggcc tgaggccaat tgtgaacatg      1980
gactacatca tggggctcg caccttccgc cgagataaga aagtgcagag actgacctca       2040
aggctgaaga cactgtttag cgtgctgaat tatgagagag ctcggagacc tagtctgctg      2100
ggagcatcaa tgctgggcct ggacgatatt caccgggcat ggagaacctt cgtgctgcga      2160
atccgggcac agaacccacc tccacagctg tactttgtga aggtcgccat tactggcgct      2220
tatgacacca tcccccagga taggctggtg gaggtcatcg cctccatcat caagcctcag      2280
gaatctacat actgcgtgag gcgctatgct gtggtccaga agactgcacg cgggcacgtg      2340
cgaaaggctt tcaaatccca tgtctctacc ctgacagacc tgcagccata catgagacag      2400
tttgtggaga ggctgcagga aacaagcccc ctgcgcgatg cagtggtcat tgagcagtct      2460
agttcactga cgaagctag ctcctctctg ttccacctgt ttctgcggct gatgcacaat       2520
catgtggtca gaatcagggg caaatcttac atccagtgtc aggggattcc ccaaggaagt      2580
atcctgtcaa ccctgctgtg cagcctgtgc tatggggaca tggagcgcaa gctgttcccc      2640
gggatccgac gggatggact gctgctgcgg ctggtggacg atttcctgct ggtcacccct      2700
cacctgacac aggcccagac tttttctgaga acccctggtga aaggcgtccc agagtacggg     2760
tgcgtggtca acctgaggaa gactgtggtc aatttcccg tggaagacgg ggctctggga       2820
tccaccgcac cactgcagct gcctgcacat ggactgtttc cttggtgtgg actgctgctg      2880
gacactagaa ccctggaggt gagttcagat tacagctcct atgcccggac ttcaattaga      2940
gctagcctga ccttctccag aggctttaag ccagggagga acatgagaag gaaactgctg      3000
gccgtgctga ggctgaagtg ccacgctctg tttctggacc tgcaggtgaa cagcatccag      3060
accgtctaca caaatatcta taaaattctg ctgctgcagg cctacagatt ccatgcttgc      3120
gtgctgcagc tgcccttcaa ccagcaggtc tggaagaatc cctccttctt tctgagagtg      3180
atcgctgata ccgcatctct gtgctatagt atcctgaagg ccaaaaatgc tggactgtct      3240
ctgggagcaa aaggagcagc tggaccactg cctagtgagg cagtgcggtg gctgtgcctg      3300
caggccttcc tgctgaagct gacaagacac agcgtgactt acgtcccact gctgggcgca      3360
ctgaggactg cccagaccca gctgtccagg cagctgcctc gcacaactct gacagccctg      3420
gaagcagccg ctaacccagc actgaccgcc gacttcaaaa caattctgga t               3471
```

<210> SEQ ID NO 5
<211> LENGTH: 3420
<212> TYPE: DNA
<213> ORGANISM: Artificial
<220> FEATURE:

<223> OTHER INFORMATION: nucleotide sequence encoding SEQ ID NO:2

<400> SEQUENCE: 5

```
atgggctggt cctgtattat tctgtttctg gtcgccaccg ctaccggagt ccatagtcct      60
agagcacccc gctgtcgcgc cgtgagggcc ctgctgagag gcaggtaccg cgaggtgctg     120
ccactggcta cctttctgcg gagactggga ccacctggca ggctgctggt gaggcgaggc     180
gaccctgcag ctttccgcgc cctggtggct cagtgcctgg tgtgcgtgcc ttggggagca     240
aggccaccac ctgcagcacc atgctttcga caggtgagct gtctgaagga gctggtcgca     300
cgagtggtcc agcgactgtg cgaaaggggc gctcgcaacg tgctggcatt cggctttgcc     360
ctgctggatg gagctcgagg aggaccacca gtggccttca ccaccagcgt gcggagctac     420
ctgcccaata ctgtgaccga gacactgagg ggatccggag catggggact gctgctgcga     480
cgagtggggg acgatgtcct gacacacctg ctggcacgct gcgccctgta tctgctggtg     540
gctccctcat gcgcatacca ggtctgtggc cctccactgt atgacctgtg cgcacctgcc     600
agcctgcccc tgcctgcccc agggctgcct ggactgccag actgccagg actgggagct     660 ggagcagggg cctcagctga tctgcgacct acccggcagg ctcagaacag cggagcaaga     720
aggcgccgag gaagtccagg atcaggagtg cctctggcaa agaggccacg agaagcgtc     780 gcatccgagc cagaacgagg agctcaccgg agcttcccta gggcacagca gccacctgtg     840
agtgaggcac ctgcagtgac tccagcagtc gctgcaagtc ctgcagcttc atgggaagga     900
ggaccaccag gaacccgacc tactaccca gcttggcatc cataccctgg accacaggga     960
gtgccacacg accctgccca tccagagacc aagcggtttc tgtattgcag cgggggacga    1020
gaacggctga gaccaagctt cctgctgtcc gccctgcctc caacactgag tggggctaga    1080
aaactggtgg agactatctt tctgggatca gctccacaga agcctggagc agcaaggcga    1140
atgcgacggc tgcctgccag gtactggagg atgcgcccac tgttccagga gctgctggga    1200
aaccacgctc gatgcccta tcgagcactg ctgcggacac attgtcctct gcgggcaatg    1260
gctgcaaagg aagggagtgg aaatcaggca caccgaggag tgggaatctg cccctggag    1320 agacctgtcg cagctccaca ggaacagacc gacagcacac gactggtgca gctgctgcgc    1380
cagcatagct ccccatggca ggtgtacgcc tttctgagag cttgcctgtg ctggctggtg    1440
ccaaccggac tgtgggggtc caggcacaac cagagaagg ttctgcgcaa tgtgaagaaa    1500
ttcatctccc tgggcaagca tgccaaactg tctctgcagg agctgacctg gaagatgaaa    1560
gtgagggact gtacatggct gcacggaaac ccaggagctt gctgcgtgcc tgcagcagaa    1620
catcgccgac gggaggaaat cctggccaga tttctggtgc tggtcgatgg acacatctac    1680
gtggtcaaac tgctgaggtc tttctttat gtgaccgaga caactttcca gaagaatagg    1740
ctgttctttt atcgcaagag cgtgtggagt aaactgcagt ctatcggcat tagacagcac    1800
ctgaaaagag tgcagctgag ggagctgagt gaggccgaag tcagacagca tagggaagct    1860
cgccctgcac tgctgacaag ccgactgcgg ttcatcccca agcctgacgg gctgcgccca    1920
attgtgaaca tggattacgt ggtcggagca cggacctta gaagggagaa acgagccgaa    1980
cggctgacat caagagtgaa ggctctgttc agcgtcctga attatgagag ggcacgccga    2040
cccggactgc tgggagcctc tgtgctgggg ctggacgaca tccacagagc ttggaggacc    2100
tttgtgctga gagtcagggc acaggacccc cctccagagc tgtacttcgt gaaggtcgca    2160
atcaccggag cctatgacac aattccacag gatcgcctgc tgaagtgat tgccagcatc    2220 atcaagcccc agaataccta ctgcgtgcgg agatatgcag tggtccagaa ggctgcacac    2280
```

51

52

-continued

```
ggccatgtgc ggaaggcctt taaatcacac gtcagcactc tgaccgatct gcagccttac      2340
atgcgccagt tcgtggctca tctgcaggag acttctccac tgcgggacgc agtggtcatc      2400
gagcagtcta gttcactgaa cgaagctagc tccgggctgt tcgacgtgtt cctgaggttc      2460
atgtgccacc atgccgtgcg cattcgagga aaatcctacg tccagtgtca gggaatccca      2520
cagggctcca ttctgtctac cctgctgtgc tctctgtgct atggcgacat ggagaataag      2580
ctgtttgcag gcatcaggcg agatggactg ctgctgagac tggtggacga ttttctgctg      2640
gtcacccccc acctgacaca tgccaaaact ttcctgcgca ccctggtgcg aggagtccct      2700
gaatacggct gcgtggtcaa cctgaggaag acagtggtca atttcccagt ggaggacgaa      2760
gccctgggag gaactgcttt tgtccagatg ccagcacacg gactgttccc atggtgtgga      2820
ctgctgctgg acacacgcac tctggaggtg cagagcgatt actctagtta tgcccggaca      2880
tctatcagag ctagtctgac ttttaaccgg gggttcaagg ccggaagaaa tatgcgacgg      2940
aaactgtttg gcgtgctgcg gctgaagtgc catagtctgt tcctggacct gcaggtgaac      3000
tcactgcaga ctgtctgtac caatatctac aaaattctgc tgctgcaggc atatagattt      3060
cacgcctgcg tgctgcagct gccattccat cagcaggtct ggaagaaccc cactttcttt      3120
ctgagagtga tcagcgatac cgctagcctg tgctactcca ttctgaaggc caaaaatgct      3180
ggaatgtccc tgggagcaaa aggagcagct ggaccactgc catctgaggc tgtgcagtgg      3240
ctgtgccacc aggcattcct gctgaagctg actcggcata gagtgaccta tgtcccactg      3300
ctgggaagcc tgcggacagc ccagactcag ctgtccagaa agctgccagg aaccacactg      3360
accgccctgg aagcagccgc taacccagct ctgcccagcg actttaaaac aatcctggat      3420
```

```
<210> SEQ ID NO 6
<211> LENGTH: 3453
<212> TYPE: DNA
<213> ORGANISM: Artificial
<220> FEATURE:
<223> OTHER INFORMATION: nucleotide sequence encoding SEQ ID NO:3

<400> SEQUENCE: 6
atgggatggt cttgtattat tctgttcctg gtcgccactg ccaccggggt ccacagccct        60
agagcaccta gatgtagagc cgtgagaagt ctgctgcgct cacactaccg agaggtgctg       120
cctctggcca cattcgtccg gagactggga ccacagggat ggcgactggt gcagagaggc       180
gatccagcag cttttagagc tctggtcgca cagtgcctgg tgtgcgtgcc atgggacgca       240
cgaccacctc cagcagcccc tagcttccgg caggtgtcct gcctgaaaga actggtggca       300
agggtcctgc agcggctgtg cgagcgagga gctaagaacg tgctggcatt cggatttgca       360
ctgctggatg gagcacgagg aggaccacct gaggccttta ccacaagcgt gcggtcctat       420
ctgcccaata cagtcactga cgctctgaga ggcagcggag catggggact gctgctgagg       480
cgagtgggcg acgatgtgct ggtccacctg ctggcacgat cgctctgtt cgtgctggtc       540 gctccttcct gcgcatacca ggtgtgcgga ccaccactgt atcagctggg agctgcaacc       600
caggcaagac ctccaccaca cgctagtgga cctcgacgga gactgggatg tgaaagggct       660
tggaaccatt cagtgcgcga ggcaggagtc ccactggac tgccagcacc tggagcaagg       720
cgccgaggag gaagtgcctc acgaagcctg ccactgccaa agcgaccacg aagaggagca       780
gctcctgaac cagagaggac tcccgtggga cagggatcct gggcacaccc aggaaggacc       840
cgcggaccct cagatagagg cttctgcgtg gtcagccctg ctaggccagc agaggaagcc       900
```

-continued

```
actagtctgg agggcgccct gtcagggacc agacactctc atcccagtgt gggcaggcag      960
caccatgctg ggcctccatc cacatctcgg cccctagac catgggatac tccctgtcca     1020
cccgtgtacg ccgaaaccaa acatttcctg tatagctccg gcgacaagga gcagctgcgc     1080
ccaagttttc tgctgtctag tctgcgacca tcactgaccg gagcaaggcg cctggtggaa     1140
acaatcttcc tgggaagcag gccctggatg cctggaactc cacgacggct gccacgactg     1200
cctcagagat actggcagat gcgccctctg tttctggagc tgctgggaaa ccacgcacag     1260
tgcccatatg gagtgctgct gaaaacacat tgtcccctga gggcagcagt gactcctgct     1320
gcaggcgtct gcgcacgaga gaagccacag ggaagcgtgg cagctccaga ggaagaggac     1380
accgatccta gaaggctggt gcagctgctg aggcagcact caagcccttg gcaggtgtac     1440
ggattcgtcc gcgcatgtct cgcccgactg gtgcctccag gactgtgggg aagccgccac     1500
aacgaacgga gattcctgcg aaataccaag aagttcatct ccctggggaa gcatgccaaa     1560
ctgtctctgc aggagctgac atggaaaatg tcagtgaggg actgcgcttg gctgaggcgc     1620
agccctggag tgggatgcgt gccagcagca gagcaccgac tgcgagaaga gattctggcc     1680
aagttcctgc attggctgat gagcgtgtac gtggtcgaac tgctgcgctc cttctttat      1740 gtcaccgaga ctacctttca gaagaacaga ctgttcttt ataggaaatc agtgtggagc       1800
cagctgcaga gcatcggcat tagacagctg ttcaatagcg tgcacctgag ggaactgtcc     1860
gaagcagagg tccgacggca tagggaggct cgaccagcac tgctgaccag ccggctgagg     1920
tttctgccca aacctagtgg actgaggccc atcgtgaaca tggattacat tatgggcgcc     1980
aggactttcc accgcgacaa gaaagtgcag catctgacct ctcagctgaa gacactgttt     2040
agtgtgctga attatgagcg agcaagaagg ccctctctgc tgggagctag tatgctgggg     2100
atggacgaca tccaccgagc atggcggacc ttcgtgctgc gcattcgagc ccagaaccca     2160
gctccccagc tgtactttgt gaaggtcgcc atcacaggag cctatgacgc tctgccacag     2220
gataggctgg tggaagtcat cgccaatgtg attcgaccac aggagtccac ctactgcgtc     2280
cggcattatg cagtggtcca gagaacagcc aggggccacg tgcgcaaggc tttcaaacga     2340
cacgtgagca ccttcgccga cctgcagcca tacatgcggc agtttgtgga aagactgcag     2400
gagaccagcc tgctgcgaga cgcagtggtc attgaacagt cctctagtct gaacgaggct     2460
ggctcaagcc tgttccacct gtttctgcgc ctggtgcaca atcatgtggt ccggatcggg     2520
ggaaagagtt acattcagtg tcagggagtg ccccagggct ccatcctgtc taccctgctg     2580
tgctccctgt gctatggcga tatggaacgc cgactgttcc ccggaattga gcaggacggc     2640
gtgctgctgc gactggtgga cgatttcctg ctggtgactc ctcatctgac ccaggcccag     2700
gcttttctgc ggacactggt gaaaggggtc cccgaatacg gatgcagagc taacctgcag     2760
aagactgcag tgaatttccc tgtcgaggac ggggccctgg gatctgctgc acctctgcag     2820
ctgccagctc actgcctgtt tccatggtgt ggcctgctgc tggatacccg gacactggag     2880
gtgagctgtg actactcctc ttatgcccat acaagcatca gagcttccct gactttctct     2940
cagggggcca gcccggaag aaacatgcgg agaaaactgc tggcagtgct gaggctgaag     3000
tgctgtgccc tgtttctgga tctgcaggtg aacggcatcc acaccgtgta catgaatgtc     3060
tataaaattt tcctgctgca ggcataccgg tttcatgcct gcgtgctgca gctgcccttc     3120
aaccagcctg tcagaaagaa tcctagcttc tttctgagag tgatcgcaga cacagccagt     3180
tgctgttatt cactgctgaa agctagaaat gcaggactgt ccctgggagc aaagggagct     3240
tcaggactgt tcccaagcga agccgctagg tggctgtgcc tgcacgcatt tctgctgaaa     3300
```

-continued

```
ctggcccacc atagcggaac ttaccgatgt ctgctgggcg ctctgcaggc agccaaggca      3360
catctgtccc gacagctgcc acgagggacc ctggctgcac tggaggcagc tgcagaccct      3420
tctctgactg ccgatttcaa aaccatcctg gac                                    3453

<210> SEQ ID NO 7
<211> LENGTH: 3399
<212> TYPE: DNA
<213> ORGANISM: Artificial
<220> FEATURE:
<223> OTHER INFORMATION: nucleotide sequence encoding SEQ ID NO:29

<400> SEQUENCE: 7
atgccgcgcg ctccccgctg ccgagccgtg cgctccctgc tgcgcagcca ctaccgcgag       60
gtgctgccgc tggccacgtt cgtgcggcgc ctggggcccc agggctggcg gctggtgcag      120
cgcggggacc cggcggcttt ccgcgcgctg gtggcccagt gcctggtgtg cgtgccctgg      180
gacgcacggc cgcccccgc cgcccctcc ttccgccagg tgtcctgcct gaaggagctg         240
gtggcccgag tgctgcagag gctgtgcgag cgcggcgcga agaacgtgct ggccttcggc       300
ttcgcgctgc tggacggggc ccgcgggggc cccccgagg ccttcaccac cagcgtgcgc        360
agctacctgc ccaacacggt gaccgacgca ctgcggggga gcgggcgtg ggggctgctg        420 ctgccgcgcg tgggcgacga cgtgctggtt cacctgctgg cacgctgcgc gctctttgtg      480
ctggtggctc ccagctgcgc ctaccaggtg tgcgggccgc cgctgtacca gctcggcgct      540
gccactcagg cccggcccc gccacacgct agtggacccc gaaggcgtct gggatgcgaa       600
cgggcctgga accatagcgt cagggaggcc ggggtccccc tgggcctgcc agccccgggt      660
gcgaggaggc gcgggggcag tgccagccga agtctgccgt tgcccaagag gcccaggcgt      720
ggcgctgccc ctgagccgga gcggacgccc gttgggcagg ggtcctgggc ccacccgggc      780
aggacgcgtg gaccgagtga ccgtggtttc tgtgtggtgt cacctgccag acccgccgaa      840
gaagccacct cttttggaggg tgcgctctct ggcacgcgcc actcccaccc atccgtgggc      900
cgccagcacc acgcgggccc cccatccaca tcgcggccac cacgtccctg ggacacgcct      960
tgtcccccgg tgtacgccga gaccaagcac ttcctctact cctcaggcga caaggagcag     1020
ctgcggccct ccttcctact cagctctctg aggcccagcc tgactggcgc tcggaggctc     1080
gtggagacca tctttctggg ttccaggccc tggatgccag ggactccccg caggttgccc     1140
cgcctgcccc agcgctactg gcaaatgcgg cccctgtttc tggagctgct tgggaaccac     1200
gcgcagtgcc cctacggggt gctcctcaag acgcactgcc cgctgcgagc tgcggtcacc     1260
ccagcagccg gtgtctgtgc ccgggagaag ccccagggct ctgtggcggc ccccgaggag     1320
gaggacacag accccgtcg cctggtgcag ctgctccgcc agcacagcag ccctggcag      1380 gtgtacggct tcgtgcgggc ctgcctgcgc cggctggtgc ccccaggcct ctggggctcc     1440
aggcacaacg aacgccgctt cctcaggaac accaagaagt catctccct ggggaagcat     1500 gccaagctct cgctgcagga gctgacgtgg aagatgagcg tgcgggactg cgcttggctg     1560
cgcaggagcc caggggttgg ctgtgttccg gccgcagagc accgtctgcg tgaggagatc     1620
ctggccaagt tcctgcactg gctgatgagt gtgtacgtcg tcgagctgct caggtctttc     1680
ttttatgtca cggagaccac gttttcaaaag aacaggctct ttttctaccg gaagagtgtc     1740
tggagcaagt tgcaaagcat tggaatcaga cagcacttga agagggtgca gctgcgggag     1800
ctgtcggaag cagaggtcag gcagcatcgg gaagccaggc ccgccctgct gacgtccaga     1860
```

```
ctccgcttca tccccaagcc tgacgggctg cggccgattg tgaacatgga ctacgtcgtg        1920
ggagccagaa cgttccgcag agaaaagagg gccgagcgtc tcacctcgag ggtgaaggca        1980
ctgttcagcg tgctcaacta cgagcgggcg cggcgccccg gcctcctggg cgcctctgtg        2040
ctgggcctgg acgatatcca cagggcctgg cgcaccttcg tgctgcgtgt gcgggcccag        2100
gacccgccgc ctgagctgta ctttgtcaag gtggatgtga cgggcgcgta cgacaccatc        2160
ccccaggaca ggctcacgga ggtcatcgcc agcatcatca aaccccagaa cacgtactgc        2220
gtgcgtcggt atgccgtggt ccagaaggcc gcccatgggc acgtccgcaa ggccttcaag        2280
agccacgtct ctaccttgac agacctccag ccgtacatgc gacagttcgt ggctcacctg        2340
caggagacca gcccgctgag ggatgccgtc gtcatcgagc agagctcctc cctgaatgag        2400
gccagcagtg gcctcttcga cgtcttccta cgcttcatgt gccaccacgc cgtgcgcatc        2460
aggggcaagt cctacgtcca gtgccagggg atcccgcagg gctccatcct ctccacgctg        2520
ctctgcagcc tgtgctacgg cgacatggag aacaagctgt ttgcggggat tcggcgggac        2580
gggctgctcc tgcgtttggt ggatgatttc ttgttggtga cacctcacct cacccacgcg        2640
aaaaccttcc tcaggaccct ggtccgaggt gtccctgagt atggctgcgt ggtgaacttg        2700
cggaagacag tggtgaactt ccctgtagaa gacgaggccc tgggtggcac ggcttttgtt        2760
cagatgccgg cccacggcct attcccctgg tgcggcctgc tgctggatac ccggaccctg        2820
gaggtgcaga gcgactactc cagctatgcc cggacctcca tcagagccag tctcaccttc        2880
aaccgcggct tcaaggctgg gaggaacatg cgtcgcaaac tctttggggt cttgcggctg        2940
aagtgtcaca gcctgtttct ggatttgcag gtgaacagcc tccagacggt gtgcaccaac        3000
atctacaaga tcctcctgct gcaggcgtac aggtttcacg catgtgtgct gcagctccca        3060
tttcatcagc aagtttggaa gaaccccaca tttttcctgc gcgtcatctc tgacacggcc        3120
tccctctgct actccatcct gaaagccaag aacgcaggga tgtcgctggg ggccaagggc        3180
gccgccggcc ctctgccctc cgaggccgtg cagtggctgt gccaccaagc attcctgctc        3240
aagctgactc gacaccgtgt cacctacgtg ccactcctgg ggtcactcag gacagcccag        3300
acgcagctga gtcggaagct cccgggggacg acgctgactg ccctggaggc cgcagccaac        3360
ccggcactgc cctcagactt caagaccatc ctggactga                               3399
```

<210> SEQ ID NO 8
<211> LENGTH: 3441
<212> TYPE: DNA
<213> ORGANISM: Artificial
<220> FEATURE:
<223> OTHER INFORMATION: nucleotide sequence encoding SEQ ID NO:30

<400> SEQUENCE: 8

```
atggacgcca tgaagagggg cctgtgctgc gtgctgctgc tgtgcggagc cgtgttcgtg          60
agccccagcg agatccccag agcccccaga tgtagggccg tgagggccct gctgaggggc         120
agatacagag aggtgctgcc cctggccacc ttcctgagaa ggctgggccc tcctggcaga         180
ctgctggtcc gcagaggcga tcctgccgcc tttagagccc tggtggccca gtgcctggtc         240
tgtgtgcctt ggggagccag acctcctcct gccgcccctt gcttcaggca ggtgtcctgc         300
ctgaaagaac tggtggccag ggtggtgcag agactgtgcg agaggggcgc cagaaacgtg         360
ctggccttcg ctttgccct gctggatggc gctagaggcg ccctcctgt ggccttcacc           420 acctccgtgc ggagctacct gcccaacacc gtgaccgaga ccctgagagg aagcggagcc         480
tggggcctgc tgctgagaag agtgggcgac gacgtgctga cccacctgct ggccagatgc         540
```

-continued

```
gccctgtacc tgctggtcgc ccctagctgt gcctaccagg tctgcggccc tcccctgtat      600
gacctgtgcg ccctgcctc tctgcctctg cctgccctg gactgcctgg cctgccaggg       660
ctgcctggac tgggagctgg cgctggcgcc tctgccgacc tgagacccac cagacaggcc      720
cagaacagcg gcgccagaag aagaagaggc agccccggaa gcggcgtgcc tctggccaag      780
aggcctcgga gaagcgtggc ctctgagccc gaaagaggcg cccacagaag cttccccaga      840
gcccagcagc ctcctgtgtc tgaggcccct gccgtgacac ctgccgtggc cgcctctcct      900
gctgcttctt gggagggcgg aacctcctgga accagaccca ccacccccgc ctggcaccct     960
tatcctggcc ctcagggcgt gcctcacgat cctgcccacc ccgagaccaa gcggttcctg     1020
tactgcagcg gcggcagaga gaggctgagg cccagcttcc tgctgtctgc cctgcctcct     1080
accctgagcg gagcccggaa actggtggag accatcttcc tgggcagcgc tcctcagaag     1140
cctggcgccg ctcggagaat gcggaggctg cccgccagat actggcggat gcggcccctg     1200
ttccaggaac tgctgggcaa ccacgccaga tgcccctaca gggccctgct gaggacccac     1260
tgccctctga gggccatggc cgccaaagag ggcagcggca accaggccca cagaggcgtg     1320
ggcatctgcc ccctggaaag acccgtggcc gctccccagg aacagaccga cagcaccagg     1380
ctggtgcagc tgctgagaca gcacagcagc ccctggcagg tgtacgcctt cctgagggcc     1440
tgcctgtgtt ggctggtgcc taccggcctg tggggcagca ggcacaacca gaggcggttt     1500
ctgaggaacg tgaagaagtt catcagcctg ggcaagcacg ccaagctgtc cctgcaggaa     1560
ctgacctgga agatgaaagt gcgggactgc acctggctgc acggcaatcc tggcgcctgt     1620
tgtgtgcctg ccgccgagca caggcggagg gaagagatcc tggcccggtt cctggtgctg     1680
gtcgatggcc acatctacgt ggtgaagctg ctgcggagct tcttctacgt gaccgagacc     1740
accttccaga aaaataggct gttcttctac cggaagagcg tgtggagcca gctgcagagc     1800
atcggcatca ggcagctgtt caacagcgtg cacctgagag agctgtccga ggccgaagtg     1860
aggcggcaca gagaggccag acccgccctg ctgaccagca ggctgagatt cctgcccaag     1920
cccagcggcc tgaggcccat cgtgaacatg gactacatca tgggcgccag gaccttccac     1980
agggacaaga aggtgcagca cctgaccagc cagctgaaaa ccctgttcag cgtgctgaac     2040
tacgagaggg ccagaaggcc tagcctgctg ggcgccagca tgctgggcat ggacgacatc     2100
cacagggcct ggcggacctt cgtgctgagg atcagggccc agaaccctgc cccccagctg     2160
tacttcgtga aggtggccat caccggcgcc tacgacgccc tgcctcagga cagactggtg     2220
gaggtgatcg ccaacgtgat caggccccag gaaagcacct actgcgtcag gcactacgcc     2280
gtggtgcaga gaaccgccag gggccacgtg aggaaggcct tcaagaggca cgtgagcacc     2340
ttcgccgacc tgcagcccta catgaggcag ttcgtggaga ggctgcagga gaccagcctg     2400
ctgagggatg ccgtggtgat cgagcagagc agcagcctga cgaggccggg cagctccctg     2460
ttccacctgt ttctgaggct ggtgcacaac cacgtggtgc ggatcggcgg caagagctac     2520
atccagtgcc agggcgtgcc tcagggcagc atcctgagca ccctgctgtg cagcctgtgc     2580
tacggcgaca tggaaaggcg gctgttccct ggcatcgagc aggacggcgt gctgctgaga     2640
ctggtggacg acttcctgct ggtgacccct catctgaccc aggcccaggc cttcctgaga     2700
accctggtga agggcgtgcc cgagtacggc tgcagggcca acctgcagaa aaccgccgtg     2760
aacttccctg tggaggacgg cgctctggga tctgctgccc ctctgcagct gcctgcccac     2820
tgcctgttcc cttggtgcgg cctgctgctg gacaccagga ccctggaagt gagctgcgac     2880
```

-continued
_____

```
tacagcagct acgcccacac cagcatcagg gccagcctga ccttcagcca gggcgccaag    2940
cccggcagga acatgcggag gaagctgctg gccgtgctga ggctgaagtg ctgcgccctg    3000
ttcctggacc tgcaggtcaa cggcatccac accgtgtaca tgaacgtgta caaaatcttc    3060
ctgctgcagg cctacaggtt ccacgcctgc gtgctgcagc tgcccttcaa ccagcccgtg    3120
aggaagaacc ccagcttctt cctgagggtg atcgccgaca ccgccagctg ctgctacagc    3180
ctgctgaagg ccagaaatgc cggcctgtct ctgggagcca agggcgccag cggcctgttt    3240
cctagcgagg ccgccagatg gctgtgcctg cacgcctttc tgctgaagct ggcccaccac    3300
agcggcacct acagatgcct gctgggagcc ctgcaggccg ccaaagccca cctgagcagg    3360
cagctgccta gaggaacact ggccgccctg gaagccgccg ctgaccctag cctgaccgcc    3420
gacttcaaga ccatcctgga c                                              3441
```

```
<210> SEQ ID NO 9
<211> LENGTH: 9
<212> TYPE: PRT
<213> ORGANISM: Homo sapiens

<400> SEQUENCE: 9

Ala Pro Arg Cys Arg Ala Val Arg Ser
1               5

<210> SEQ ID NO 10
<211> LENGTH: 9
<212> TYPE: PRT
<213> ORGANISM: Canis familiaris

<400> SEQUENCE: 10

Ala Pro Arg Cys Arg Ala Val Arg Ala
1               5

<210> SEQ ID NO 11
<211> LENGTH: 9
<212> TYPE: PRT
<213> ORGANISM: Homo sapiens

<400> SEQUENCE: 11

Glu Val Leu Pro Leu Ala Thr Phe Val
1               5

<210> SEQ ID NO 12
<211> LENGTH: 9
<212> TYPE: PRT
<213> ORGANISM: Canis familiaris

<400> SEQUENCE: 12

Glu Val Leu Pro Leu Ala Thr Phe Leu
1               5

<210> SEQ ID NO 13
<211> LENGTH: 9
<212> TYPE: PRT
<213> ORGANISM: Homo sapiens

<400> SEQUENCE: 13

Val Glu Leu Leu Arg Ser Phe Phe Tyr
1               5

<210> SEQ ID NO 14
<211> LENGTH: 9
<212> TYPE: PRT
```

-continued

```
<213> ORGANISM: Canis familiaris

<400> SEQUENCE: 14

Val Lys Leu Leu Arg Ser Phe Phe Tyr
1               5

<210> SEQ ID NO 15
<211> LENGTH: 9
<212> TYPE: PRT
<213> ORGANISM: Homo sapiens

<400> SEQUENCE: 15

Leu Leu Thr Ser Arg Leu Arg Phe Ile
1               5

<210> SEQ ID NO 16
<211> LENGTH: 9
<212> TYPE: PRT
<213> ORGANISM: Canis familiaris

<400> SEQUENCE: 16

Leu Leu Thr Ser Arg Leu Arg Phe Leu
1               5

<210> SEQ ID NO 17
<211> LENGTH: 9
<212> TYPE: PRT
<213> ORGANISM: Homo sapiens

<400> SEQUENCE: 17

Arg Pro Ile Val Asn Met Asp Tyr Val
1               5

<210> SEQ ID NO 18
<211> LENGTH: 9
<212> TYPE: PRT
<213> ORGANISM: Canis familiaris

<400> SEQUENCE: 18

Arg Pro Ile Val Asn Met Asp Tyr Ile
1               5

<210> SEQ ID NO 19
<211> LENGTH: 9
<212> TYPE: PRT
<213> ORGANISM: Homo sapiens

<400> SEQUENCE: 19

Lys Ala Leu Phe Ser Val Leu Asn Tyr
1               5

<210> SEQ ID NO 20
<211> LENGTH: 9
<212> TYPE: PRT
<213> ORGANISM: Canis familiaris

<400> SEQUENCE: 20

Lys Thr Leu Phe Ser Val Leu Asn Tyr
1               5

<210> SEQ ID NO 21
<211> LENGTH: 9
<212> TYPE: PRT
<213> ORGANISM: Homo sapiens
```

<400> SEQUENCE: 21

Gly Leu Asp Asp Ile His Arg Ala Trp
1               5

<210> SEQ ID NO 22
<211> LENGTH: 9
<212> TYPE: PRT
<213> ORGANISM: Canis familiaris

<400> SEQUENCE: 22

Gly Met Asp Asp Ile His Arg Ala Trp
1               5

<210> SEQ ID NO 23
<211> LENGTH: 9
<212> TYPE: PRT
<213> ORGANISM: Homo sapiens

<400> SEQUENCE: 23

Ala Trp Arg Thr Phe Val Leu Arg Val
1               5

<210> SEQ ID NO 24
<211> LENGTH: 9
<212> TYPE: PRT
<213> ORGANISM: Canis familiaris

<400> SEQUENCE: 24

Ala Trp Arg Thr Phe Val Leu Arg Ile
1               5

<210> SEQ ID NO 25
<211> LENGTH: 9
<212> TYPE: PRT
<213> ORGANISM: Homo sapiens

<400> SEQUENCE: 25

Ser Pro Leu Arg Asp Ala Val Val Ile
1               5

<210> SEQ ID NO 26
<211> LENGTH: 9
<212> TYPE: PRT
<213> ORGANISM: Canis familiaris

<400> SEQUENCE: 26

Ser Leu Leu Arg Asp Ala Val Val Ile
1               5

<210> SEQ ID NO 27
<211> LENGTH: 69
<212> TYPE: DNA
<213> ORGANISM: Artificial Sequence
<220> FEATURE:
<223> OTHER INFORMATION: nucleotide sequence encoding SEQ ID NO:28

<400> SEQUENCE: 27
atggatgcaa tgaagagagg gctctgctgt gtgctgctgc tgtgtggagc agtcttcgtt      60
tcgcccagc                                                             69

<210> SEQ ID NO 28
<211> LENGTH: 23
<212> TYPE: PRT
<213> ORGANISM: Artificial Sequence

```
<220> FEATURE:
<223> OTHER INFORMATION: Tissue Plasminogen Activator (TPA)

<400> SEQUENCE: 28

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 29
<211> LENGTH: 1132
<212> TYPE: PRT
<213> ORGANISM: Homo sapiens

<400> SEQUENCE: 29

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320
```

-continued

```
Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
```

-continued

```
                    740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
        980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130
```

<210> SEQ ID NO 30

```
<211> LENGTH: 1125
<212> TYPE: PRT
<213> ORGANISM: Canis familiaris

<400> SEQUENCE: 30

Met Pro Arg Ala Pro Arg Cys Arg Ala Val Arg Ala Leu Leu Arg Gly
1               5                   10                  15

Arg Tyr Arg Glu Val Leu Pro Leu Ala Thr Phe Leu Arg Arg Leu Gly
                20                  25                  30

Pro Pro Gly Arg Leu Leu Val Arg Arg Gly Asp Pro Ala Ala Phe Arg
            35                  40                  45

Ala Leu Val Ala Gln Cys Leu Val Cys Val Pro Trp Gly Ala Arg Pro
        50                  55                  60

Pro Pro Ala Ala Pro Cys Phe Arg Gln Val Ser Cys Leu Lys Glu Leu
65                  70                  75                  80

Val Ala Arg Val Val Gln Arg Leu Cys Glu Arg Gly Ala Arg Asn Val
                85                  90                  95

Leu Ala Phe Gly Phe Ala Leu Leu Asp Gly Ala Arg Gly Gly Pro Pro
                100                 105                 110

Val Ala Phe Thr Thr Ser Val Arg Ser Tyr Leu Pro Asn Thr Val Thr
            115                 120                 125

Glu Thr Leu Arg Gly Ser Gly Ala Trp Gly Leu Leu Leu Arg Arg Val
    130                 135                 140

Gly Asp Asp Val Leu Thr His Leu Leu Ala Arg Cys Ala Leu Tyr Leu
145                 150                 155                 160

Leu Val Ala Pro Ser Cys Ala Tyr Gln Val Cys Gly Pro Pro Leu Tyr
                165                 170                 175

Asp Leu Cys Ala Pro Ala Ser Leu Pro Leu Pro Ala Pro Gly Leu Pro
            180                 185                 190

Gly Leu Pro Gly Leu Pro Gly Leu Gly Ala Gly Ala Gly Ala Ser Ala
            195                 200                 205

Asp Leu Arg Pro Thr Arg Gln Ala Gln Asn Ser Gly Ala Arg Arg Arg
    210                 215                 220

Arg Gly Ser Pro Gly Ser Gly Val Pro Leu Ala Lys Arg Pro Arg Arg
225                 230                 235                 240

Ser Val Ala Ser Glu Pro Glu Arg Gly Ala His Arg Ser Phe Pro Arg
                245                 250                 255

Ala Gln Gln Pro Pro Val Ser Glu Ala Pro Ala Val Thr Pro Ala Val
            260                 265                 270

Ala Ala Ser Pro Ala Ala Ser Trp Glu Gly Gly Pro Pro Gly Thr Arg
            275                 280                 285

Pro Thr Thr Pro Ala Trp His Pro Tyr Pro Gly Pro Gln Gly Val Pro
    290                 295                 300

His Asp Pro Ala His Pro Glu Thr Lys Arg Phe Leu Tyr Cys Ser Gly
305                 310                 315                 320

Gly Arg Glu Arg Leu Arg Pro Ser Phe Leu Leu Ser Ala Leu Pro Pro
                325                 330                 335

Thr Leu Ser Gly Ala Arg Lys Leu Val Glu Thr Ile Phe Leu Gly Ser
            340                 345                 350

Ala Pro Gln Lys Pro Gly Ala Ala Arg Arg Met Arg Arg Leu Pro Ala
            355                 360                 365

Arg Tyr Trp Arg Met Arg Pro Leu Phe Gln Glu Leu Leu Gly Asn His
    370                 375                 380

Ala Arg Cys Pro Tyr Arg Ala Leu Leu Arg Thr His Cys Pro Leu Arg
```

-continued

```
385            390            395            400

Ala Met Ala Ala Lys Glu Gly Ser Gly Asn Gln Ala His Arg Gly Val
            405            410            415

Gly Ile Cys Pro Leu Glu Arg Pro Val Ala Ala Pro Gln Glu Gln Thr
            420            425            430

Asp Ser Thr Arg Leu Val Gln Leu Leu Arg Gln His Ser Ser Pro Trp
            435            440            445

Gln Val Tyr Ala Phe Leu Arg Ala Cys Leu Cys Trp Leu Val Pro Thr
            450            455            460

Gly Leu Trp Gly Ser Arg His Asn Gln Arg Arg Phe Leu Arg Asn Val
465            470            475            480

Lys Lys Phe Ile Ser Leu Gly Lys His Ala Lys Leu Ser Leu Gln Glu
            485            490            495

Leu Thr Trp Lys Met Lys Val Arg Asp Cys Thr Trp Leu His Gly Asn
            500            505            510

Pro Gly Ala Cys Cys Val Pro Ala Ala Glu His Arg Arg Arg Glu Glu
            515            520            525

Ile Leu Ala Arg Phe Leu Val Leu Val Asp Gly His Ile Tyr Val Val
            530            535            540

Lys Leu Leu Arg Ser Phe Phe Tyr Val Thr Glu Thr Thr Phe Gln Lys
545            550            555            560

Asn Arg Leu Phe Phe Tyr Arg Lys Ser Val Trp Ser Gln Leu Gln Ser
            565            570            575

Ile Gly Ile Arg Gln Leu Phe Asn Ser Val His Leu Arg Glu Leu Ser
            580            585            590

Glu Ala Glu Val Arg Arg His Arg Glu Ala Arg Pro Ala Leu Leu Thr
            595            600            605

Ser Arg Leu Arg Phe Leu Pro Lys Pro Ser Gly Leu Arg Pro Ile Val
            610            615            620

Asn Met Asp Tyr Ile Met Gly Ala Arg Thr Phe His Arg Asp Lys Lys
625            630            635            640

Val Gln His Leu Thr Ser Gln Leu Lys Thr Leu Phe Ser Val Leu Asn
            645            650            655

Tyr Glu Arg Ala Arg Arg Pro Ser Leu Leu Gly Ala Ser Met Leu Gly
            660            665            670

Met Asp Asp Ile His Arg Ala Trp Arg Thr Phe Val Leu Arg Ile Arg
            675            680            685

Ala Gln Asn Pro Ala Pro Gln Leu Tyr Phe Val Lys Val Ala Ile Thr
            690            695            700

Gly Ala Tyr Asp Ala Leu Pro Gln Asp Arg Leu Val Glu Val Ile Ala
705            710            715            720

Asn Val Ile Arg Pro Gln Glu Ser Thr Tyr Cys Val Arg His Tyr Ala
            725            730            735

Val Val Gln Arg Thr Ala Arg Gly His Val Arg Lys Ala Phe Lys Arg
            740            745            750

His Val Ser Thr Phe Ala Asp Leu Gln Pro Tyr Met Arg Gln Phe Val
            755            760            765

Glu Arg Leu Gln Glu Thr Ser Leu Leu Arg Asp Ala Val Val Ile Glu
            770            775            780

Gln Ser Ser Ser Leu Asn Glu Ala Gly Ser Ser Leu Phe His Leu Phe
785            790            795            800

Leu Arg Leu Val His Asn His Val Val Arg Ile Gly Gly Lys Ser Tyr
            805            810            815
```

-continued

```
Ile Gln Cys Gln Gly Val Pro Gln Gly Ser Ile Leu Ser Thr Leu Leu
            820                 825                 830

Cys Ser Leu Cys Tyr Gly Asp Met Glu Arg Arg Leu Phe Pro Gly Ile
            835                 840                 845

Glu Gln Asp Gly Val Leu Leu Arg Leu Val Asp Asp Phe Leu Leu Val
            850                 855                 860

Thr Pro His Leu Thr Gln Ala Gln Ala Phe Leu Arg Thr Leu Val Lys
865                 870                 875                 880

Gly Val Pro Glu Tyr Gly Cys Arg Ala Asn Leu Gln Lys Thr Ala Val
                885                 890                 895

Asn Phe Pro Val Glu Asp Gly Ala Leu Gly Ser Ala Ala Pro Leu Gln
            900                 905                 910

Leu Pro Ala His Cys Leu Phe Pro Trp Cys Gly Leu Leu Leu Asp Thr
            915                 920                 925

Arg Thr Leu Glu Val Ser Cys Asp Tyr Ser Ser Tyr Ala His Thr Ser
    930                 935                 940

Ile Arg Ala Ser Leu Thr Phe Ser Gln Gly Ala Lys Pro Gly Arg Asn
945                 950                 955                 960

Met Arg Arg Lys Leu Leu Ala Val Leu Arg Leu Lys Cys Cys Ala Leu
                965                 970                 975

Phe Leu Asp Leu Gln Val Asn Gly Ile His Thr Val Tyr Met Asn Val
            980                 985                 990

Tyr Lys Ile Phe Leu Leu Gln Ala  Tyr Arg Phe His Ala  Cys Val Leu
        995                 1000                1005

Gln Leu  Pro Phe Asn Gln Pro  Val Arg Lys Asn Pro  Ser Phe Phe
    1010                1015                1020

Leu Arg  Val Ile Ala Asp Thr  Ala Ser Cys Cys Tyr  Ser Leu Leu
    1025                1030                1035

Lys Ala  Arg Asn Ala Gly Leu  Ser Leu Gly Ala Lys  Gly Ala Ser
    1040                1045                1050

Gly Leu  Phe Pro Ser Glu Ala  Ala Arg Trp Leu Cys  Leu His Ala
    1055                1060                1065

Phe Leu  Leu Lys Leu Ala His  His Ser Gly Thr Tyr  Arg Cys Leu
    1070                1075                1080

Leu Gly  Ala Leu Gln Ala Ala  Lys Ala His Leu Ser  Arg Gln Leu
    1085                1090                1095

Pro Arg  Gly Thr Leu Ala Ala  Leu Glu Ala Ala Ala  Asp Pro Ser
    1100                1105                1110

Leu Thr  Ala Asp Phe Lys Thr  Ile Leu Asp Ser Arg
    1115                1120                1125
```

```
<210> SEQ ID NO 31
<211> LENGTH: 498
<212> TYPE: DNA
<213> ORGANISM: Artificial Sequence
<220> FEATURE:
<223> OTHER INFORMATION: nucleotide sequence encoding PFTG

<400> SEQUENCE: 31
tctagaagcg actgggaccc cgtggtgaag gaatggctgg tggacaccgg ctactgctgt      60
gccggcggaa tcgccaacgc cgaggatggc gtggtgttcg ccgctgcagc cgacgatgac     120
gacggctgga gcaagctgta caaggacgac cacgaggagg acaccatcgg cgaggacggc     180
aacgcctgtg gcaaggtgtc catcaacgag gccagcacca tcaaggccgc cgtggacgac     240
```

-continued

```
ggcagcgccc ccaacggagt gtggatcggc ggccagaaat acaaggttgt gaggcccgag    300
aagggcttcg agtacaacga ctgtaccttc gacatcacca tgtgtgccag aagcaaaggc    360
ggagcccacc tgatcaagac ccccaacggc agcatcgtga tcgccctgta cgacgaggag    420
aaggagcagg acaagggcaa cagcagaacc agcgccctgg ccttcgccga gtacctgcac    480
cagagcggct actgatga                                                   498
```